United States Patent
Cohn et al.

(10) Patent No.: US 9,055,799 B2
(45) Date of Patent: Jun. 16, 2015

(54) ISOLATION BOX FOR PROTECTING READING MATERIAL

(76) Inventors: Elizabeth E. Cohn, Bellaire, TX (US); William E. Cohn, Bellaire, TX (US)

( * ) Notice: Subject to any disclaimer, the term of this patent is extended or adjusted under 35 U.S.C. 154(b) by 132 days.

(21) Appl. No.: 11/973,045

(22) Filed: Oct. 4, 2007

(65) Prior Publication Data
US 2008/0203103 A1    Aug. 28, 2008

Related U.S. Application Data

(60) Provisional application No. 60/849,297, filed on Oct. 4, 2006.

(51) Int. Cl.
| | |
|---|---|
| B65D 6/40 | (2006.01) |
| A61G 11/00 | (2006.01) |
| A45C 11/22 | (2006.01) |
| B25J 21/02 | (2006.01) |
| A61L 2/26 | (2006.01) |
| A61G 10/00 | (2006.01) |
| A45C 13/02 | (2006.01) |

(52) U.S. Cl.
CPC .................. *A45C 11/22* (2013.01); *B25J 21/02* (2013.01); *A61L 2/26* (2013.01); *A61G 11/009* (2013.01); *A61G 10/005* (2013.01); *A45C 13/02* (2013.01)

(58) Field of Classification Search
CPC ......... B25J 21/02; A61L 2/26; A61G 11/009; A61G 10/005
USPC ........ 220/661, 676, 914, DIG. 13; 435/303.1, 435/809; 600/21–22; D24/163
See application file for complete search history.

(56) References Cited

U.S. PATENT DOCUMENTS

| | | | | |
|---|---|---|---|---|
| 2,039,490 | A | * | 5/1936 | Mikelson ........................ 312/1 |
| 2,473,033 | A | * | 6/1949 | Letac .............................. 600/21 |
| 2,600,240 | A | * | 6/1952 | Grieb ............................. 600/22 |
| 2,695,605 | A | * | 11/1954 | Gibbon .......................... 600/22 |
| 2,786,740 | A | * | 3/1957 | Taylor et al. ..................... 312/1 |
| 3,051,163 | A | * | 8/1962 | Trexler ............................ 312/1 |
| 3,070,086 | A | * | 12/1962 | Smith et al. .................... 600/22 |
| 3,084,684 | A | * | 4/1963 | Saunders ......................... 312/1 |
| 3,088,627 | A | * | 5/1963 | Saunders ......................... 312/1 |
| 3,267,830 | A | * | 8/1966 | Van Gaasbeek .............. 454/370 |
| 3,326,203 | A | * | 6/1967 | Goertzel ......................... 600/22 |
| 3,381,414 | A | * | 5/1968 | Brown ........................... 49/281 |
| 3,410,619 | A | * | 11/1968 | Delnay et al. .................... 312/1 |
| 3,415,582 | A | * | 12/1968 | Trexler ............................ 312/1 |
| 3,907,389 | A | * | 9/1975 | Cox et al. ........................ 312/1 |
| 4,059,903 | A | * | 11/1977 | Piet et al. ......................... 312/1 |
| 4,111,753 | A | * | 9/1978 | Folsom et al. ................... 435/3 |
| 4,335,712 | A | * | 6/1982 | Trexler ........................... 600/21 |
| 4,566,293 | A | * | 1/1986 | Arner et al. .................... 62/51.1 |
| 4,697,854 | A | * | 10/1987 | Lunsford .................... 312/223.5 |

(Continued)

*Primary Examiner* — Anthony Stashick
*Assistant Examiner* — Ned A Walker
(74) *Attorney, Agent, or Firm* — Pandiscio & Pandiscio

(57) ABSTRACT

A portable reverse isolation box (PRIB) for protecting an object from the environment and/or protecting a user from the object. The PRIB includes a housing comprising a container and a lid, wherein the container has structural integrity and at least a portion of the lid is transparent, and further wherein the housing forms an airtight and watertight isolation bay when the lid is mounted on the container; a port formed in the container; and a disposable flexible element mounted in the port in an airtight and watertight relationship, the flexible element being capable of assuming a concave configuration so as to permit a user to manipulate the object within the isolation bay without opening the lid.

15 Claims, 30 Drawing Sheets

(56) References Cited

U.S. PATENT DOCUMENTS

| | | | |
|---|---|---|---|
| 4,773,392 A * | 9/1988 | Koch | 600/22 |
| 4,876,773 A * | 10/1989 | Wade | 27/23.1 |
| 4,920,768 A * | 5/1990 | Cares et al. | 68/18 R |
| 4,960,143 A * | 10/1990 | Dore et al. | 134/199 |
| 5,299,243 A * | 3/1994 | Picco | 376/287 |
| 5,316,541 A * | 5/1994 | Fischer | 600/21 |
| 5,316,733 A * | 5/1994 | Rune et al. | 422/104 |
| 5,342,121 A * | 8/1994 | Koria | 312/1 |
| 5,380,077 A * | 1/1995 | Puschner et al. | 312/1 |
| 5,594,200 A * | 1/1997 | Ramsey | 174/382 |
| 5,685,771 A * | 11/1997 | Kleppen | 454/56 |
| 5,704,381 A * | 1/1998 | Millan et al. | 134/102.2 |
| 5,711,705 A * | 1/1998 | Krainiak et al. | 454/57 |
| 5,997,928 A * | 12/1999 | Kaish et al. | 426/418 |
| 6,106,403 A * | 8/2000 | Zemel | 472/126 |
| 6,241,328 B1 | 6/2001 | Ziff | 312/1 |
| 6,367,518 B2 * | 4/2002 | Duncan | 141/97 |
| 6,428,122 B1 * | 8/2002 | Henry et al. | 312/1 |
| 6,485,467 B1 * | 11/2002 | Crook et al. | 604/174 |
| 6,592,026 B2 * | 7/2003 | Vilardi | 232/17 |
| 6,660,227 B2 * | 12/2003 | Lopez Ordaz | 422/24 |
| D485,366 S * | 1/2004 | Hauville | D24/234 |
| 6,685,622 B2 * | 2/2004 | O'Connor et al. | 600/21 |
| 6,708,697 B1 * | 3/2004 | Ziff | 132/73 |
| 6,793,617 B2 * | 9/2004 | Ford et al. | 600/21 |
| D497,429 S * | 10/2004 | Tetrault et al. | D24/163 |
| 6,851,769 B2 * | 2/2005 | Hauville | 312/1 |
| 6,968,993 B1 * | 11/2005 | Russell | 232/17 |
| 6,974,197 B1 * | 12/2005 | Henry et al. | 312/1 |
| 7,077,486 B2 * | 7/2006 | Tattershall | 312/1 |
| D567,948 S * | 4/2008 | Tierney et al. | D24/163 |
| 7,393,373 B1 * | 7/2008 | Krippner et al. | 55/385.2 |
| 7,469,977 B2 * | 12/2008 | Hauville | 312/1 |
| 2002/0045796 A1 * | 4/2002 | O'Connor et al. | 600/21 |
| 2002/0187080 A1 * | 12/2002 | Mellor et al. | 422/120 |
| 2003/0021723 A1 * | 1/2003 | Lopez Ordaz | 422/24 |
| 2003/0070404 A1 * | 4/2003 | Calabrese | 55/385.2 |
| 2003/0075594 A1 * | 4/2003 | Vilardi | 232/17 |
| 2003/0076011 A1 * | 4/2003 | Brownfiel, Jr. | 312/1 |
| 2003/0103881 A1 * | 6/2003 | Lane et al. | 422/292 |
| 2003/0127952 A1 * | 7/2003 | Friedenbach | 312/1 |
| 2003/0137225 A1 * | 7/2003 | Hauville | 312/1 |
| 2004/0116770 A1 * | 6/2004 | O'Connor et al. | 600/21 |
| 2004/0158121 A1 * | 8/2004 | Ford et al. | 600/21 |
| 2005/0244300 A1 * | 11/2005 | Hauville | 422/99 |
| 2006/0119232 A1 * | 6/2006 | Tattershall | 312/1 |
| 2006/0131516 A1 * | 6/2006 | Roberts | 250/507.1 |
| 2007/0248354 A1 * | 10/2007 | Hetnarski | 396/429 |
| 2009/0093671 A1 * | 4/2009 | Maloney | 600/21 |
| 2010/0044372 A1 * | 2/2010 | Kournikakis et al. | 220/9.2 |

* cited by examiner

ISOLATION BOX FOR PROTECTING READING MATERIAL

REFERENCE TO PENDING PRIOR PATENT APPLICATION

This patent application claims benefit of pending prior U.S. Provisional Patent Application Ser. No. 60/849,297, filed Oct. 4, 2006 by William E. Cohn et al. for PORTABLE REVERSE ISOLATION BOX (PRIB), which application is hereby incorporated herein by reference.

FIELD OF THE INVENTION

This invention relates to enclosures in general, and more particularly to an enclosure for protecting the contents of the enclosure from the environment and/or for protecting the user from the contents of the enclosure, particularly when performing recreational and household tasks.

BACKGROUND OF THE INVENTION

In many cases it is desirable to protect an object from the environment, and/or to protect the user from an object, particularly when performing recreational and household tasks. By way of example but not limitation, it can be desirable to protect a book from bath water, or to protect a cook from onion fumes.

SUMMARY OF THE INVENTION

This invention is a portable reverse isolation box (PRIB) for home use to facilitate common recreational and household tasks where a reverse isolation system will be beneficial to protect the contents of the PRIB from the environment, and/or to protect the user (and/or bystanders and/or the environment) from the contents of the PRIB.

In one preferred form of the present invention, there is provided a portable reverse isolation box (PRIB) for protecting an object from the environment and/or protecting a user from the object, the PRIB comprising:

a housing comprising a container and a lid, wherein the container has structural integrity and at least a portion of the lid is transparent, and further wherein the housing forms an airtight and watertight isolation bay when the lid is mounted on the container;

a port formed in the container; and a disposable flexible element mounted in the port in an airtight and watertight relationship, the flexible element being capable of assuming a concave configuration so as to permit a user to manipulate the object within the isolation bay without opening the lid.

In another form of the present invention, there is provided a method for utilizing a portable reverse isolation box (PRIB), the method comprising:

providing a portable reverse isolation box (PRIB) for protecting an object from the environment and/or protecting a user from the object, the PRIB comprising:

a housing comprising a container and a lid, wherein the container has structural integrity and at least a portion of the lid is transparent, and further wherein the housing forms an airtight and watertight isolation bay when the lid is mounted on the container;

a port formed in the container; and a disposable flexible element adapted to be mounted in the port in an airtight and watertight relationship, the flexible element being capable of assuming a concave configuration so as to permit a user to manipulate the object within the isolation bay without opening the lid;

placing the object in the container;

mounting the lid on the container;

compressing the housing so as to reduce the volume of the isolation bay, and maintaining the housing in the compressed condition;

mounting the disposable flexible element in the port in an airtight and watertight relationship; and releasing the housing so that the disposable flexible element is drawn into the interior of the isolation bay in a concave configuration.

In an additional form of the present invention, there is provided a method for utilizing a portable reverse isolation box (PRIB), the method comprising:

providing a portable reverse isolation box (PRIB) for protecting an object from the environment and/or protecting a user from the object, the PRIB comprising:

a housing comprising a container and a lid, wherein the container has structural integrity and at least a portion of the lid is transparent, and further wherein the housing forms an airtight and watertight isolation bay when the lid is mounted on the container;

a port formed in the container; and a disposable flexible element adapted to be mounted in the port in an airtight and watertight relationship, the flexible element being capable of assuming a concave configuration so as to permit a user to manipulate the object within the isolation bay without opening the lid;

removing the disposable flexible element from the port; and mounting a fresh disposable flexible element in the port.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
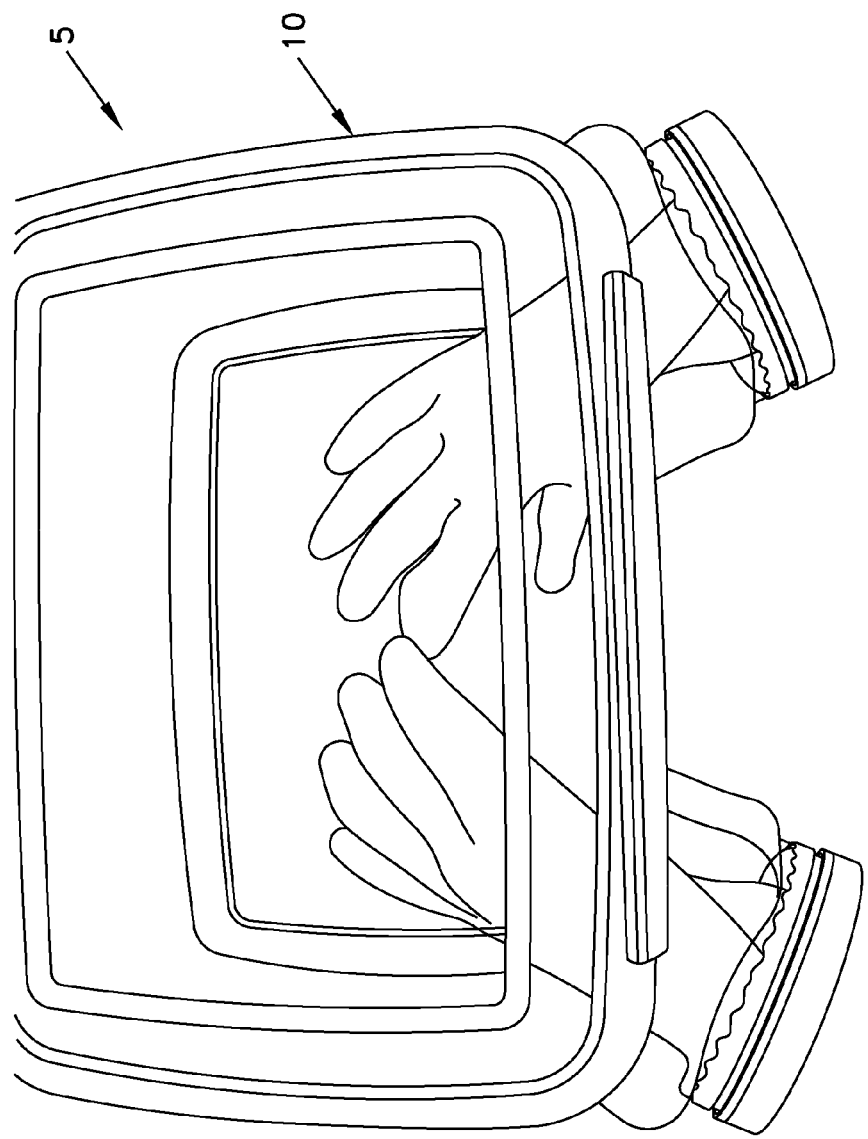
FIG. 1 is a schematic view showing a novel portable reverse isolation box (PRIB) formed in accordance with the present invention, wherein the PRIB has its lid closed.
Figure 2:
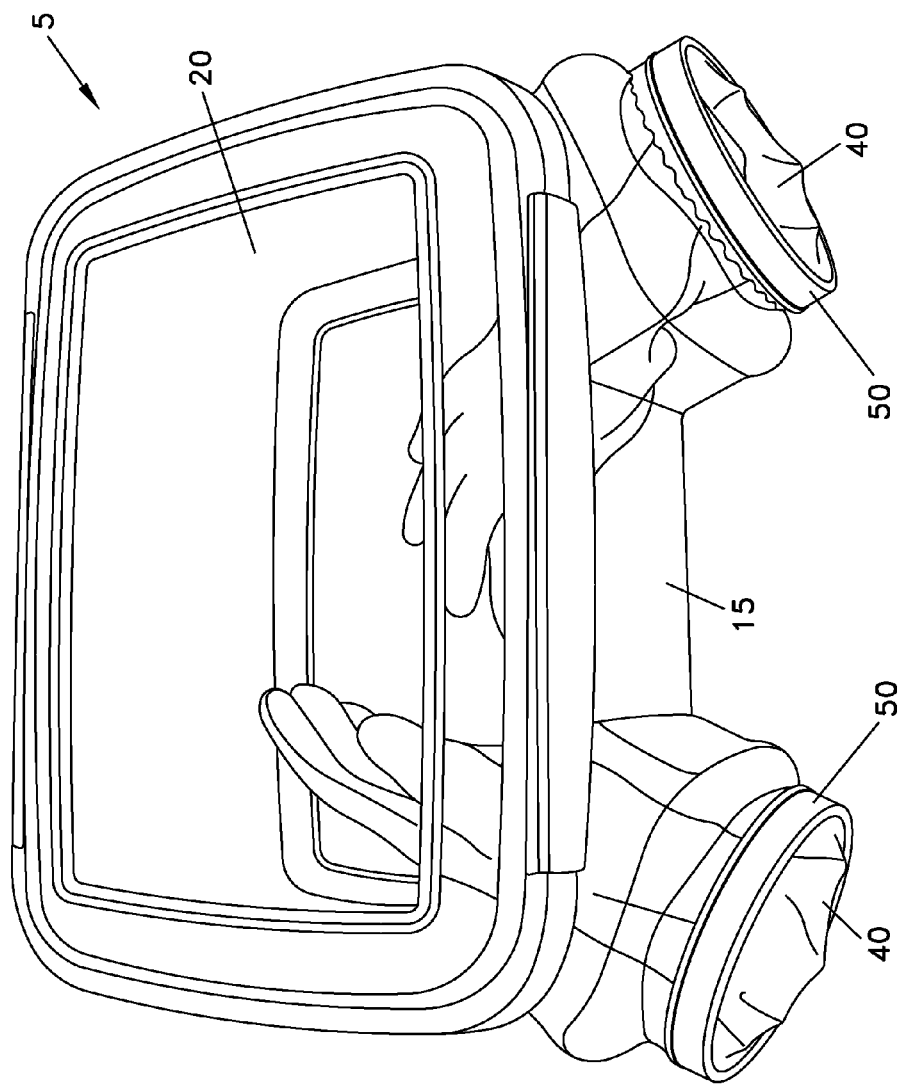
FIG. 2 is another schematic view showing the novel portable reverse isolation box (PRIB) formed in accordance with the present invention, wherein the PRIB has its lid closed.
Figure 3:
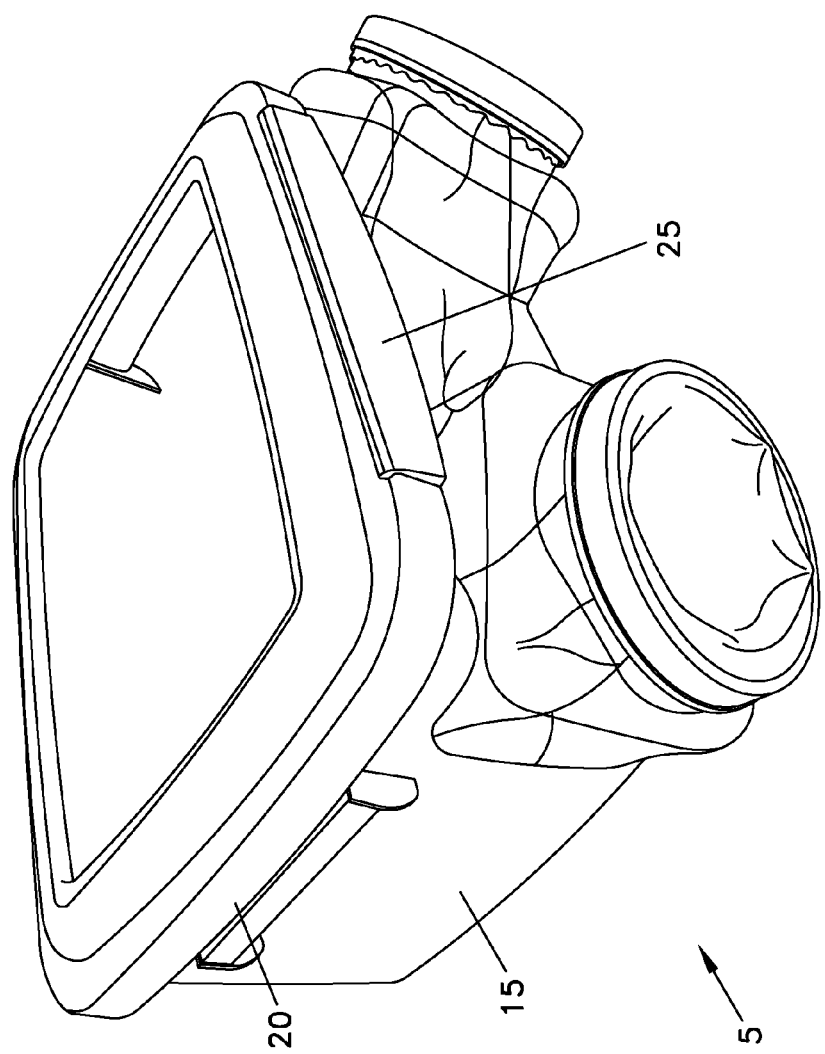
FIG. 3 is another schematic view showing the novel portable reverse isolation box (PRIB) formed in accordance with the present invention, wherein the PRIB has its lid closed.

Looking now at the drawings, there is shown a portable reverse isolation box (PRIB) 5 formed in accordance with the present invention. PRIB 5 comprises a main housing 10. More particularly, main housing 10 comprises an airtight/watertight container 15 with a transparent lid 20 which allows the contents of the PRIB to be easily seen and manipulated. Lid 20 is provided with a closure 25 for selectively closing off the interior of container 15.

Container 15 is of a size which is adequate to accommodate the item which the user is trying to protect, and/or from which the user is trying to be isolated from. The interior of container 15 is the isolation bay 30. For example, a PRIB designed to facilitate reading a paperback book in a tub or a bath, in or by the pool, or at the beach, without incurring cumulative water damage to the book, has an isolation bay 30 which is large enough to hold the desired book with the book open and to provide sufficient room to turn the pages easily. Furthermore, isolation bay 30 of PRIB 5 is of an appropriate geometry so as to allow an item to be manipulated in the desired fashion. In a preferred construction, isolation bay 30 is also of an appropriate geometry to limit the ability of an item to shift or be moved in an undesirable fashion. For example, a PRIB 5 designed for a paperback book preferably has an isolation bay 30 of limited depth as a means of keeping the pages from flipping spontaneously, and as a means of keeping the book from spontaneously closing or flipping over when PRIB 5 is transported.

It is important to note that, although main housing 10 of PRIB 5 is shown with a "box-like" geometry, any appropriate geometry may be used, with aspects of main housing 10 composed of rigid, semi-rigid, or flexible material to optimize a specific PRIB 5 for its intended use.

Figure 4:
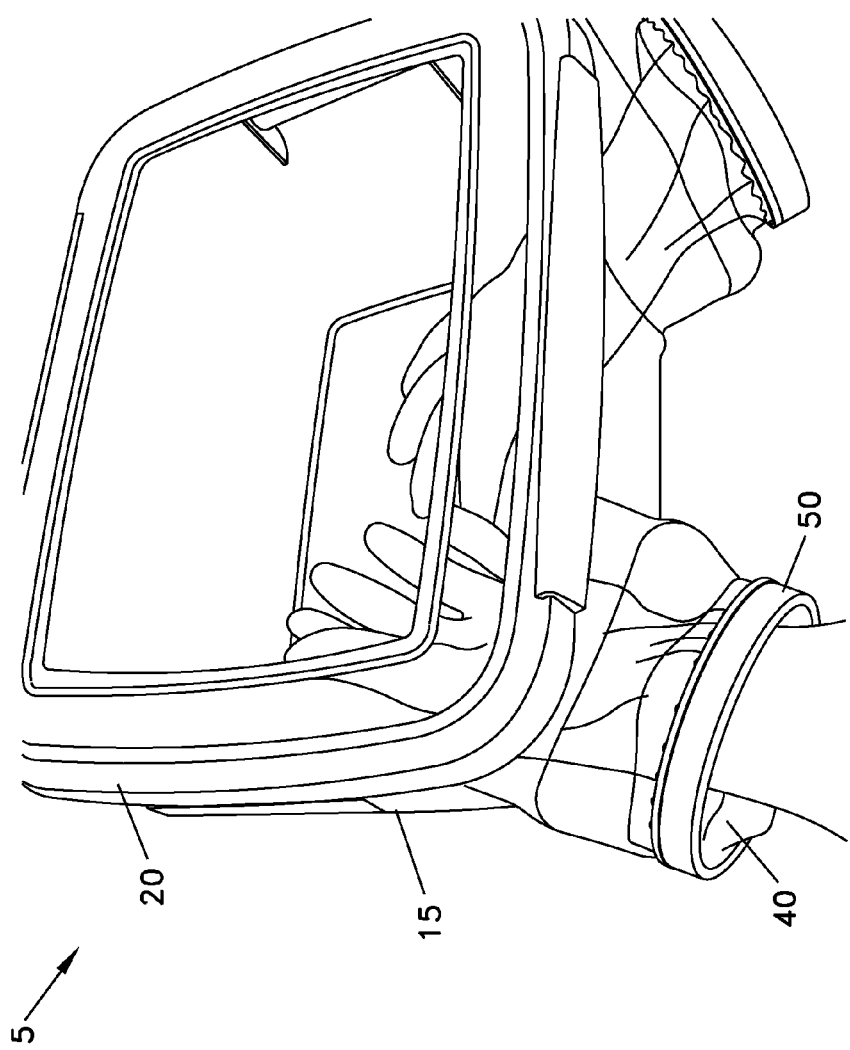
FIG. 4 is another schematic view showing the novel portable reverse isolation box (PRIB) formed in accordance with the present invention, wherein the PRIB has its lid closed.
Figure 18:
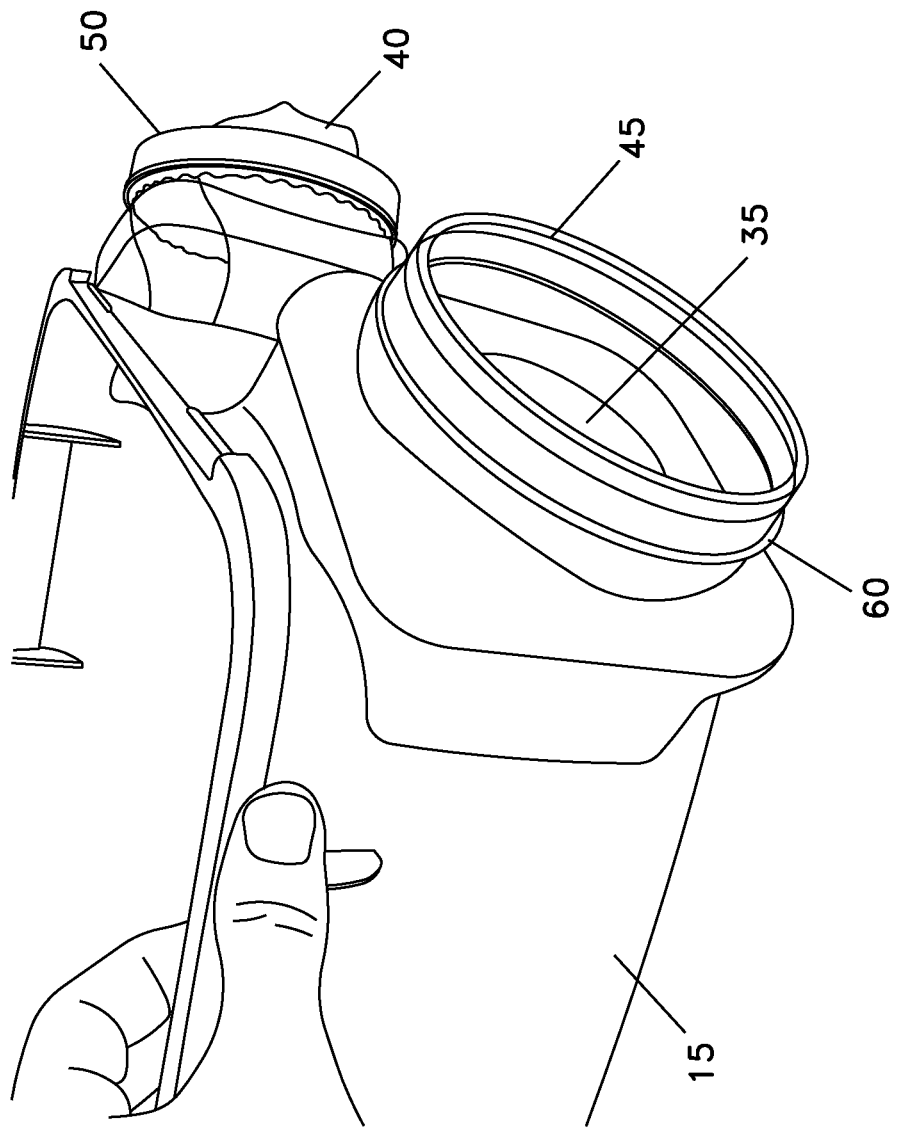
FIG. 18 is a schematic view showing details of the main housing, ports, and disposable gloves of the PRIB shown in FIGS. 1, 2, 3 and 4.
Figure 19:
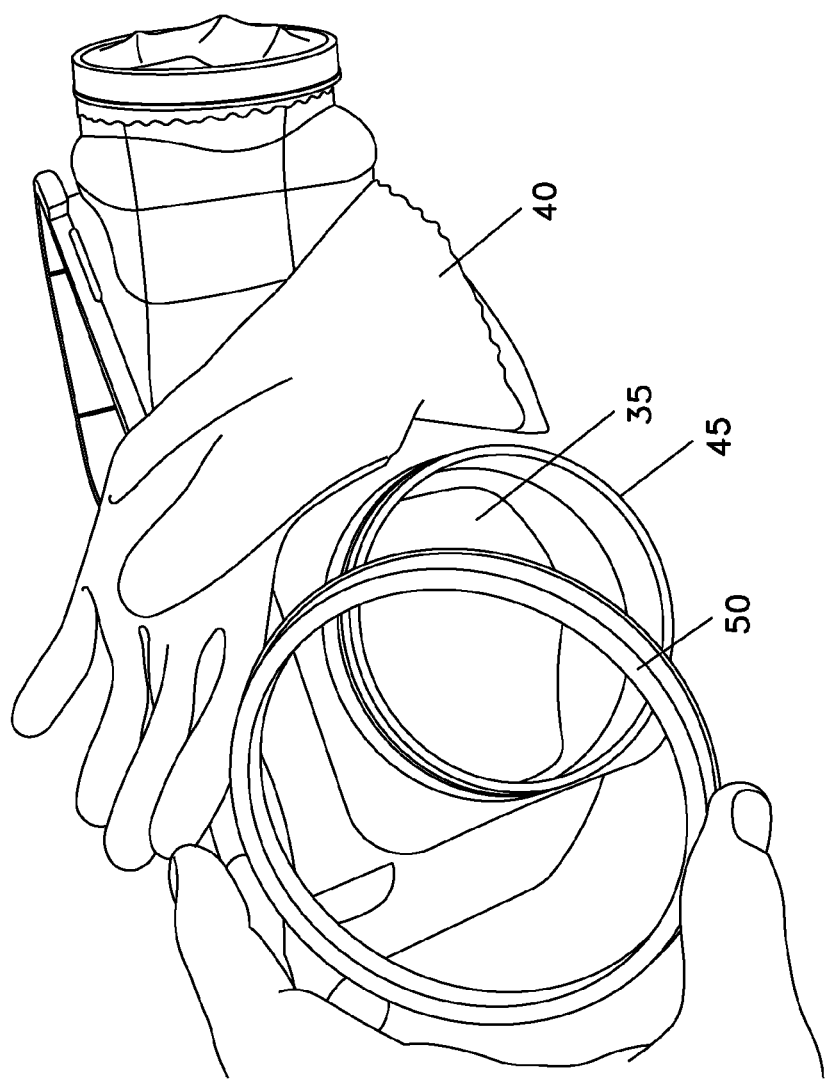
FIG. 19 is a schematic view showing details of the main housing, ports, and disposable gloves of the PRIB shown in FIGS. 1, 2, 3 and 4.
Figure 20:
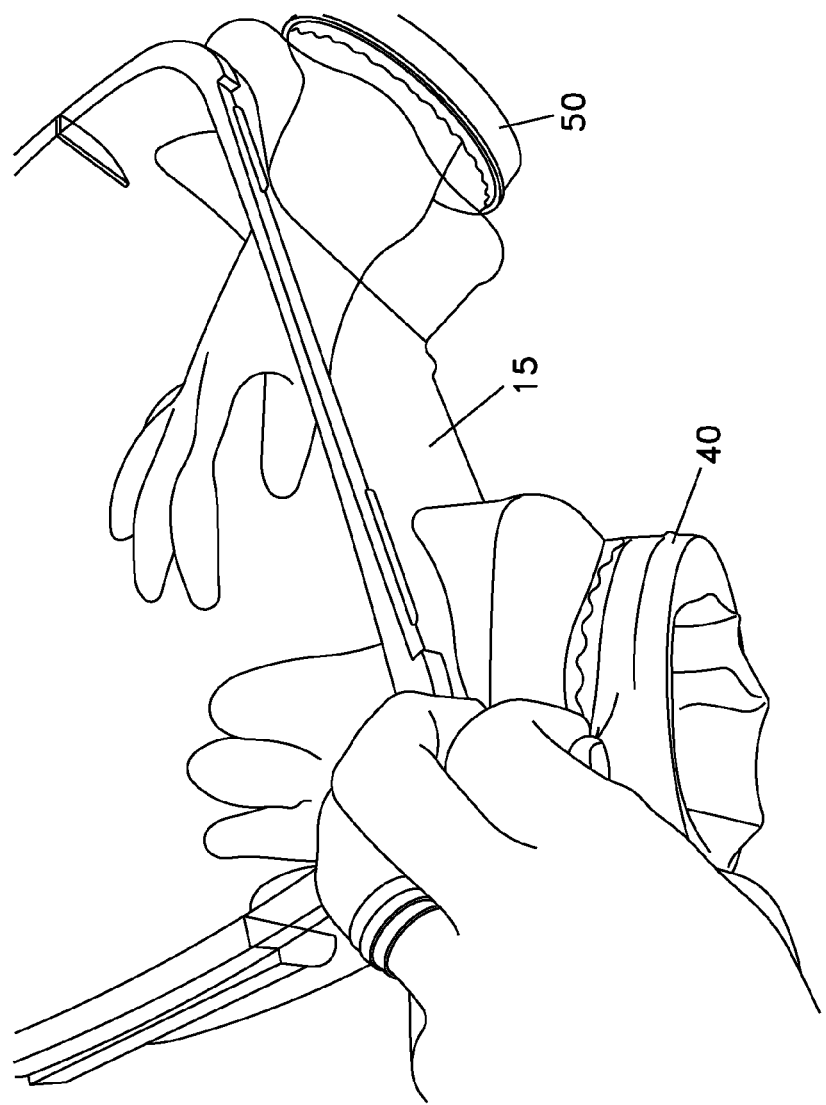
FIG. 20 is a schematic view showing details of the main housing, ports, and disposable gloves of the PRIB shown in FIGS. 1, 2, 3 and 4.
Figure 21:
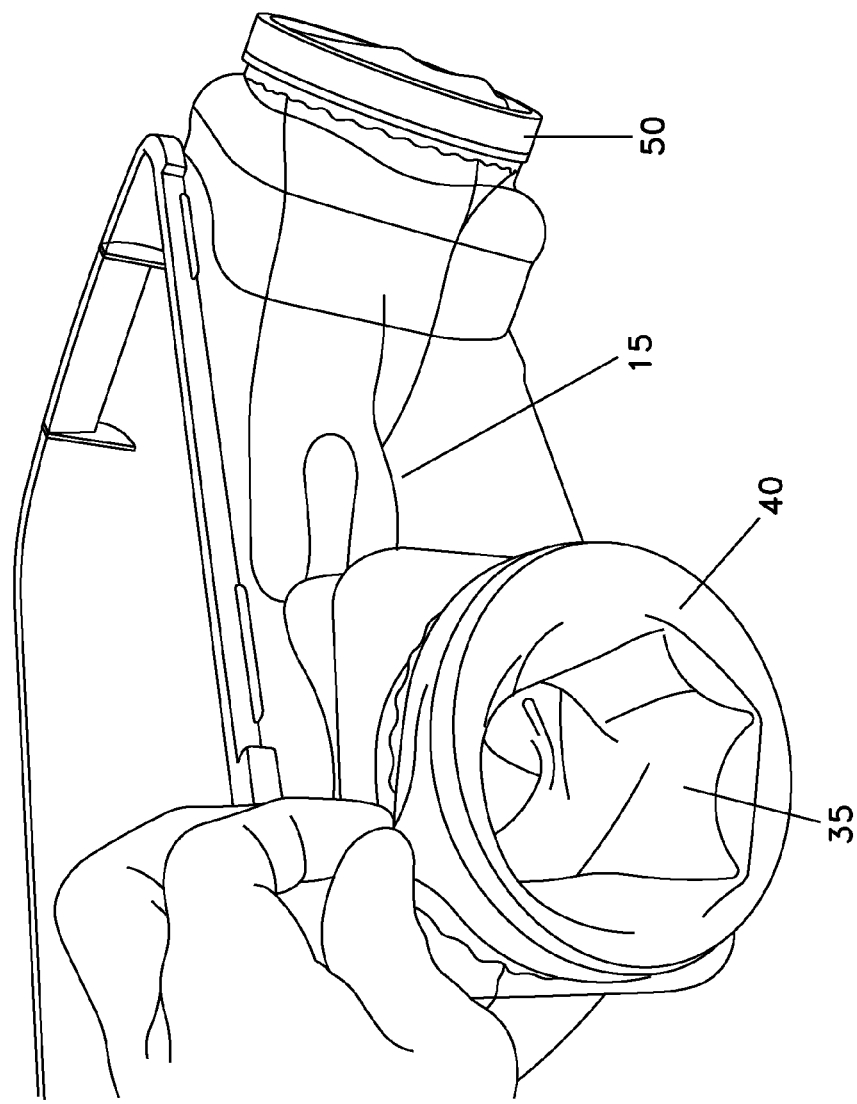
FIG. 21 is a schematic view showing details of the main housing, ports, and disposable gloves of the PRIB shown in FIGS. 1, 2, 3 and 4.
Figure 22:
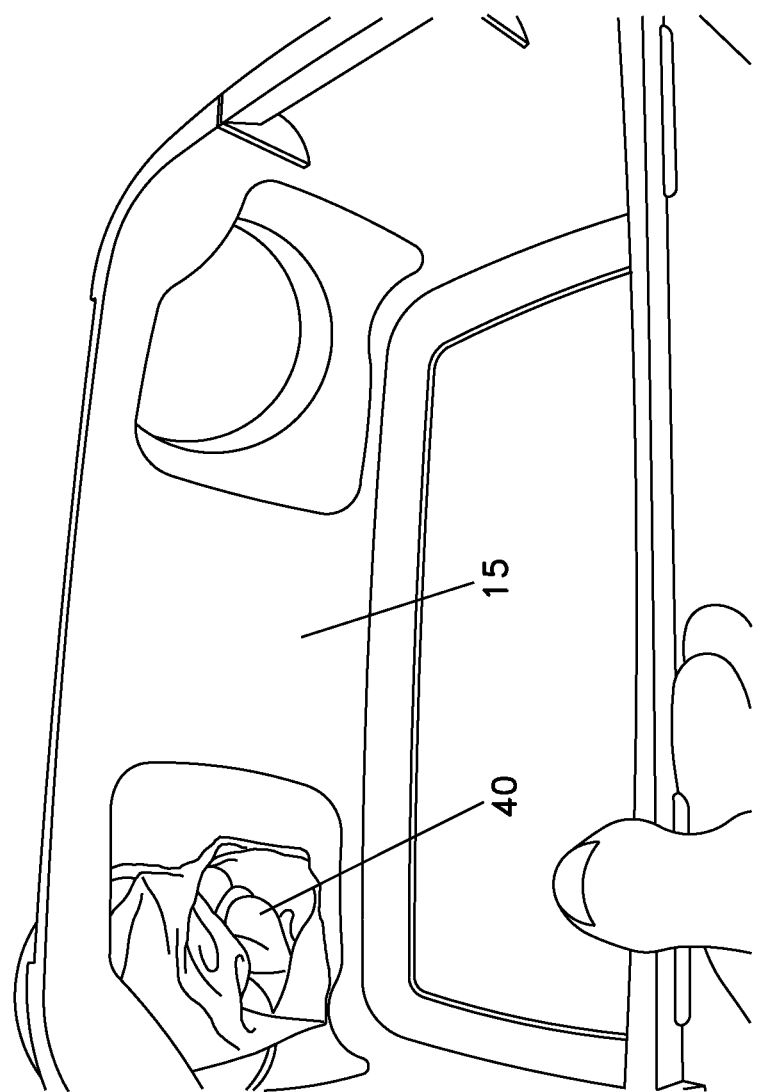
FIG. 22 is a schematic view showing details of the main housing, ports, and disposable gloves of the PRIB shown in FIGS. 1, 2, 3 and 4.
Figure 23:
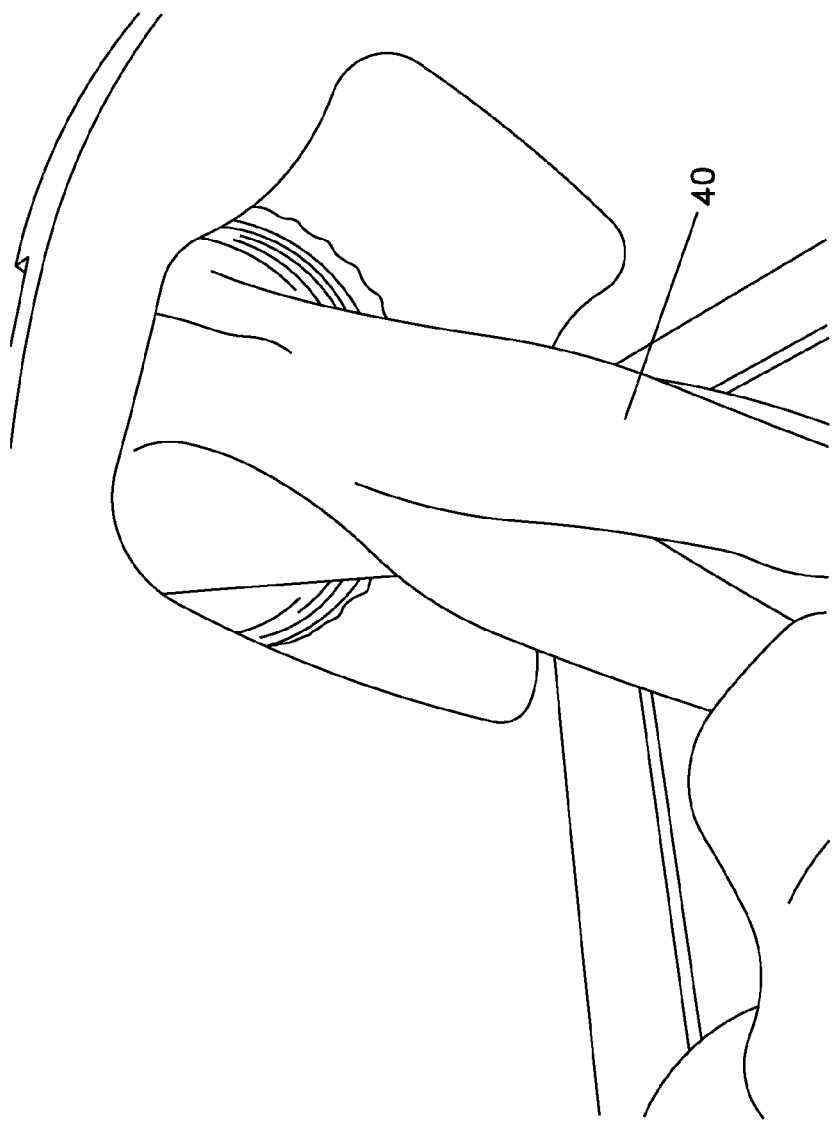
FIG. 23 is a schematic view showing details of the main housing, ports, and disposable gloves of the PRIB shown in FIGS. 1, 2, 3 and 4.
Figure 24:
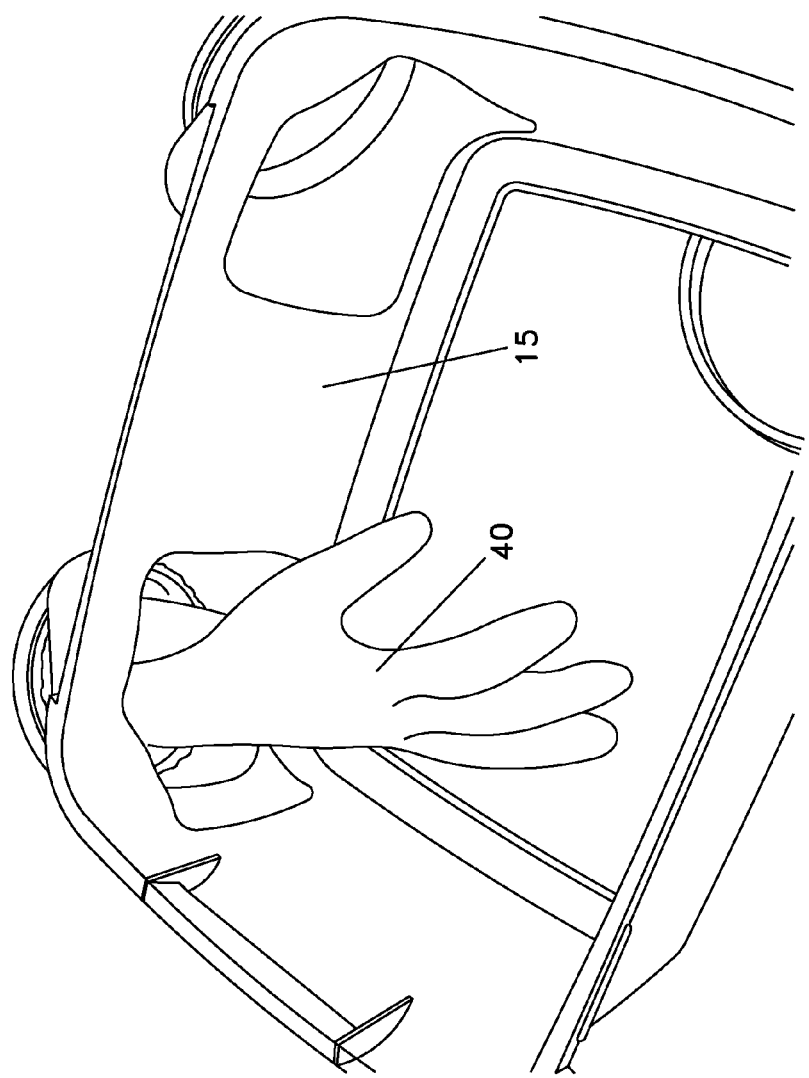
FIG. 24 is a schematic view showing details of the main housing, ports, and disposable gloves of the PRIB shown in FIGS. 1, 2, 3 and 4.
Figure 25:
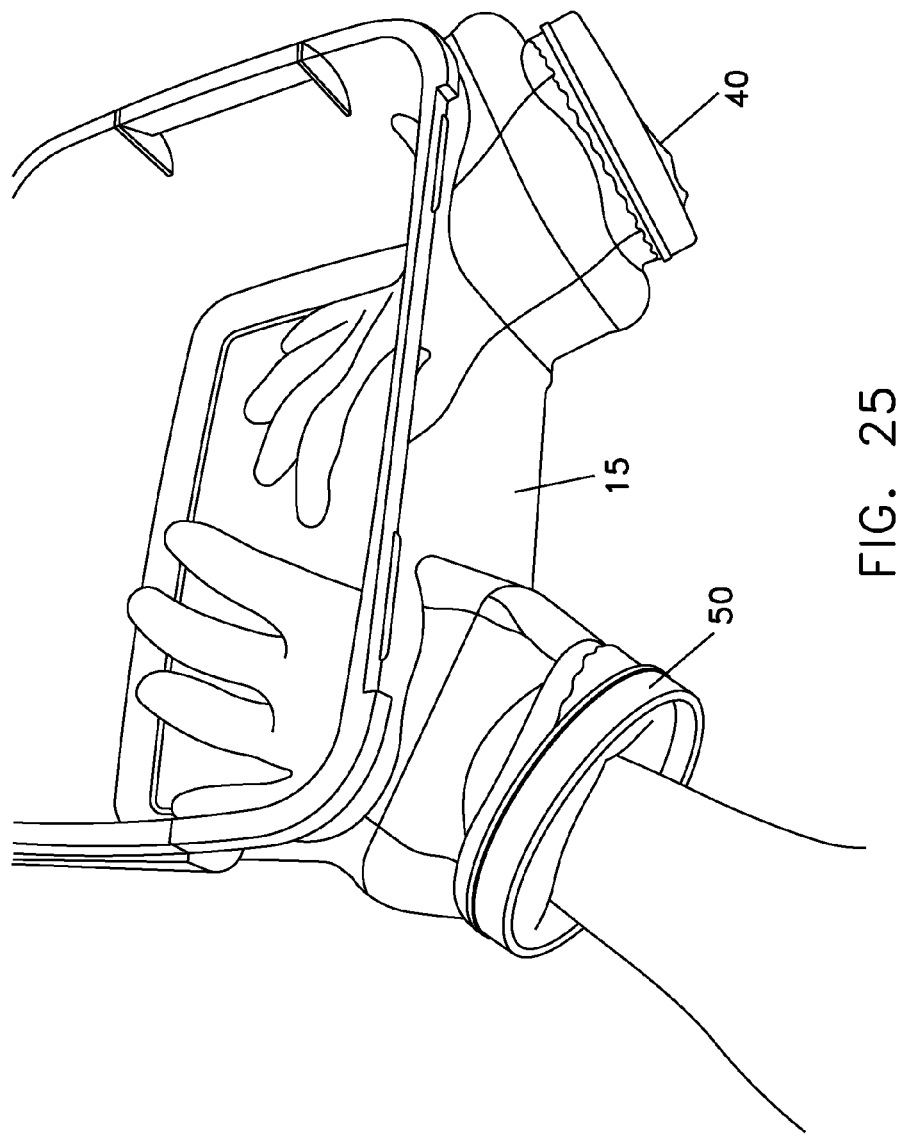
FIG. 25 is a schematic view showing details of the main housing, ports, and disposable gloves of the PRIB shown in FIGS. 1, 2, 3 and 4.
Figure 26:
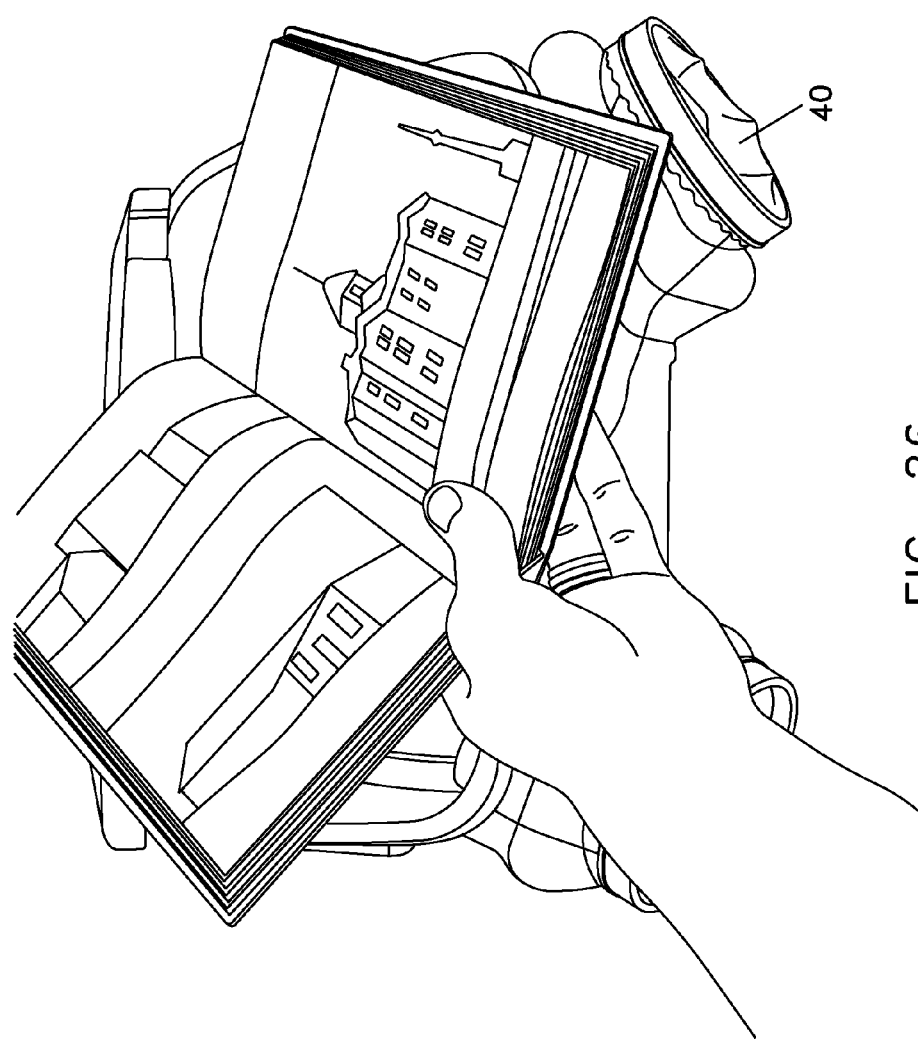
FIG. 26 is another schematic view showing details of the main housing, ports, and disposable gloves of the PRIB shown in FIGS. 1, 2, 3 and 4.
Figure 27:
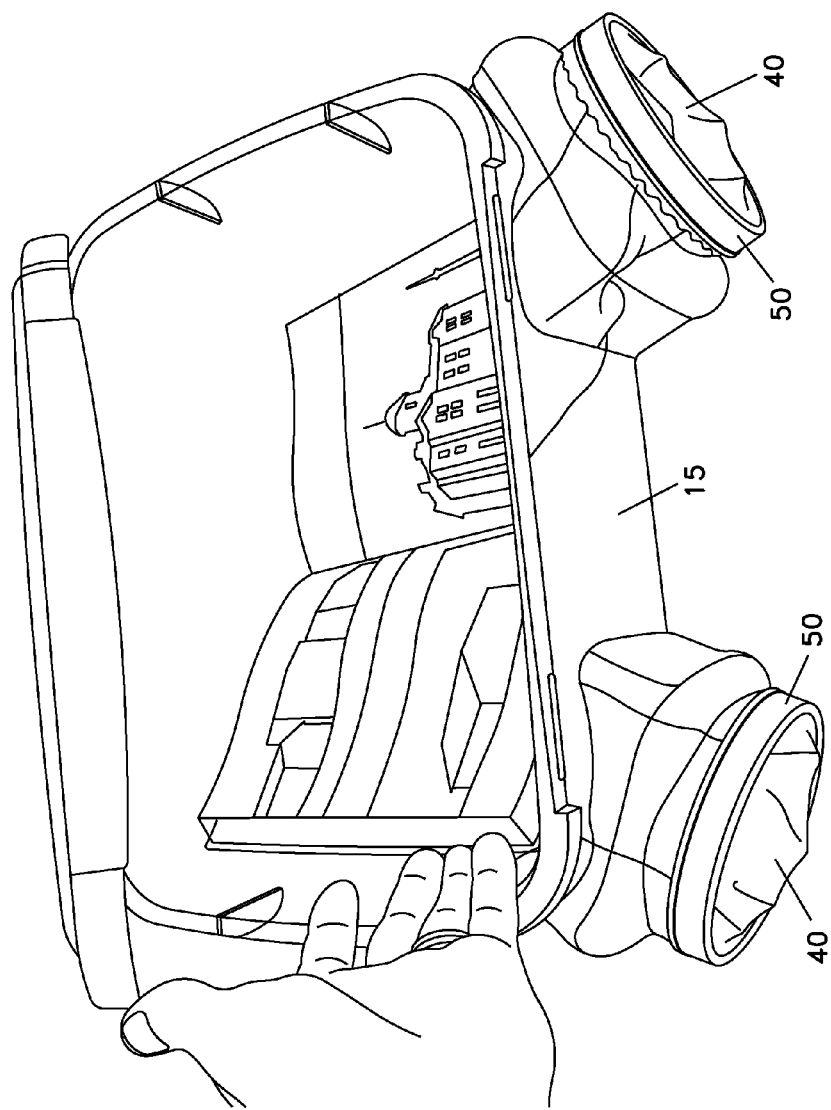
FIG. 27 is a schematic view showing reading material being placed in the PRIB of FIGS. 1, 2, 3 and 4.
Figure 28:
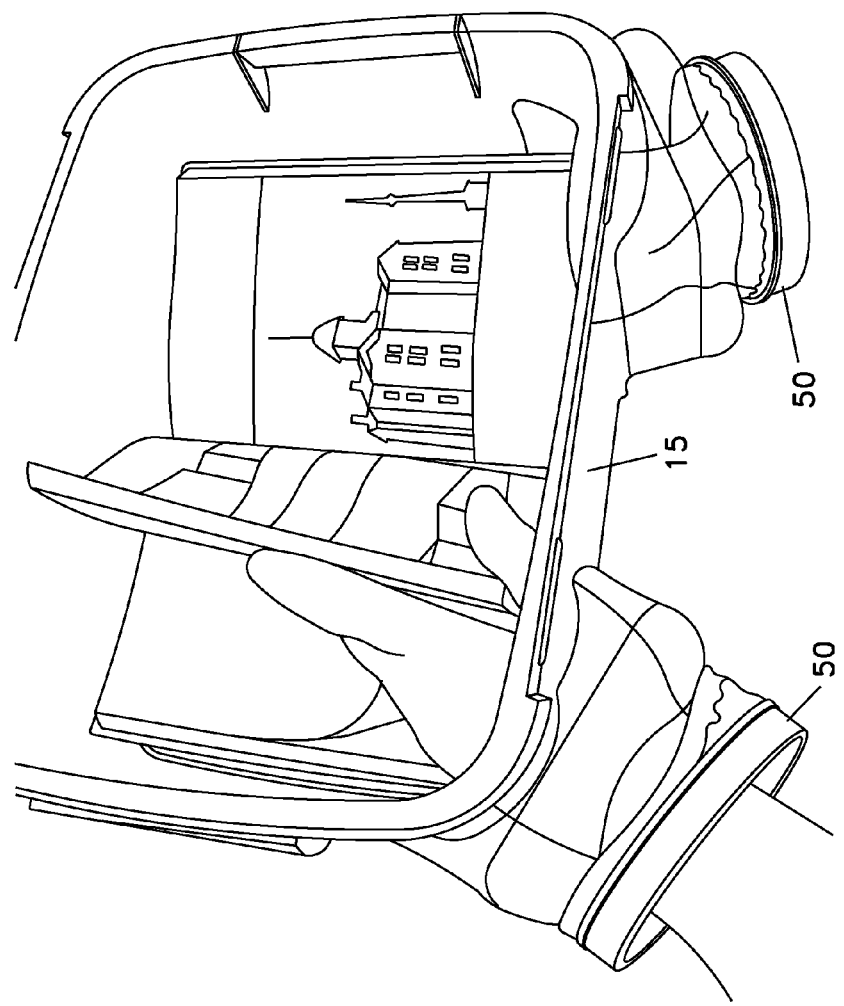
FIG. 28 is a schematic view showing reading material being placed in the PRIB of FIGS. 1, 2, 3 and 4.
Figure 29:
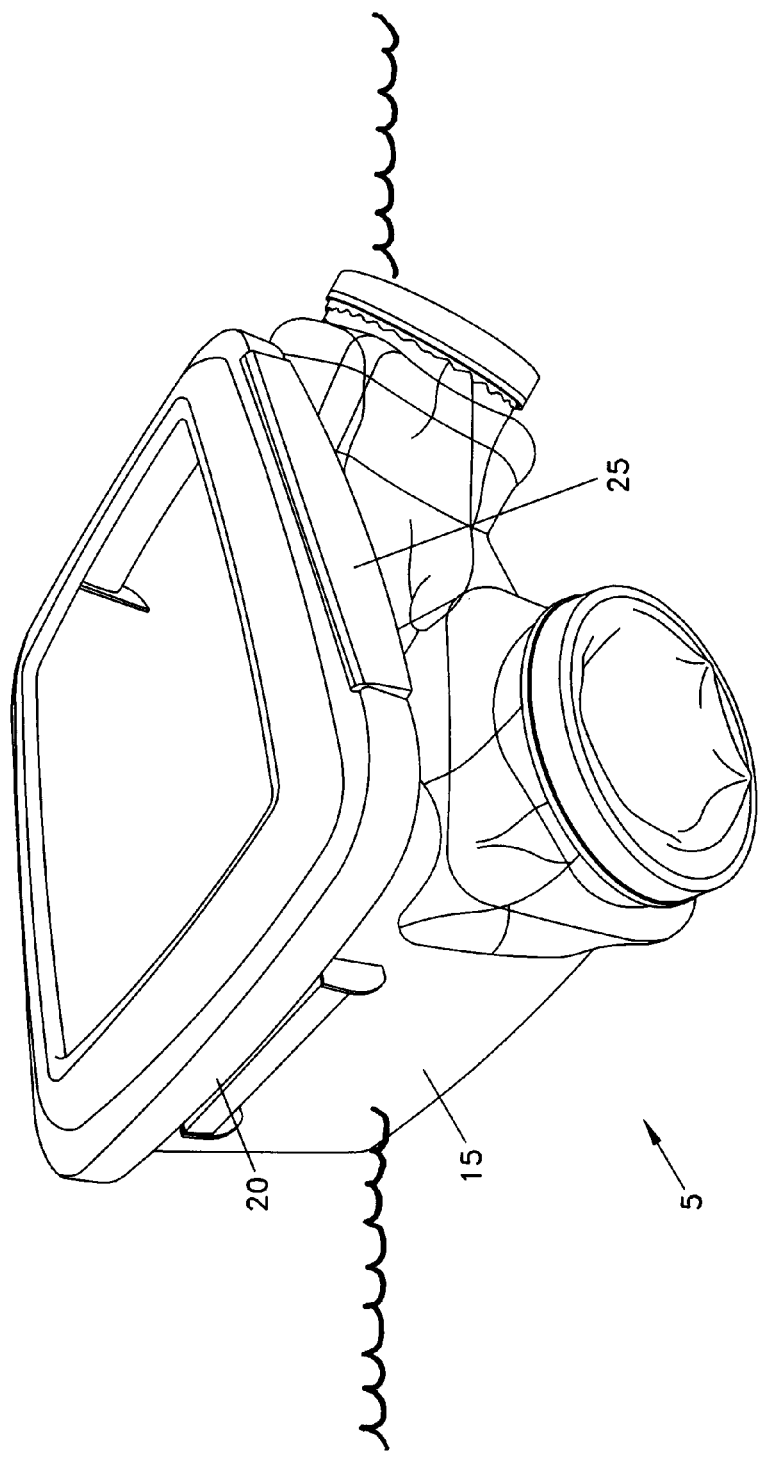
FIG. 29 is a schematic view showing the PRIB of FIGS. 1, 2, 3 and 4 floating in water.
Figure 30:
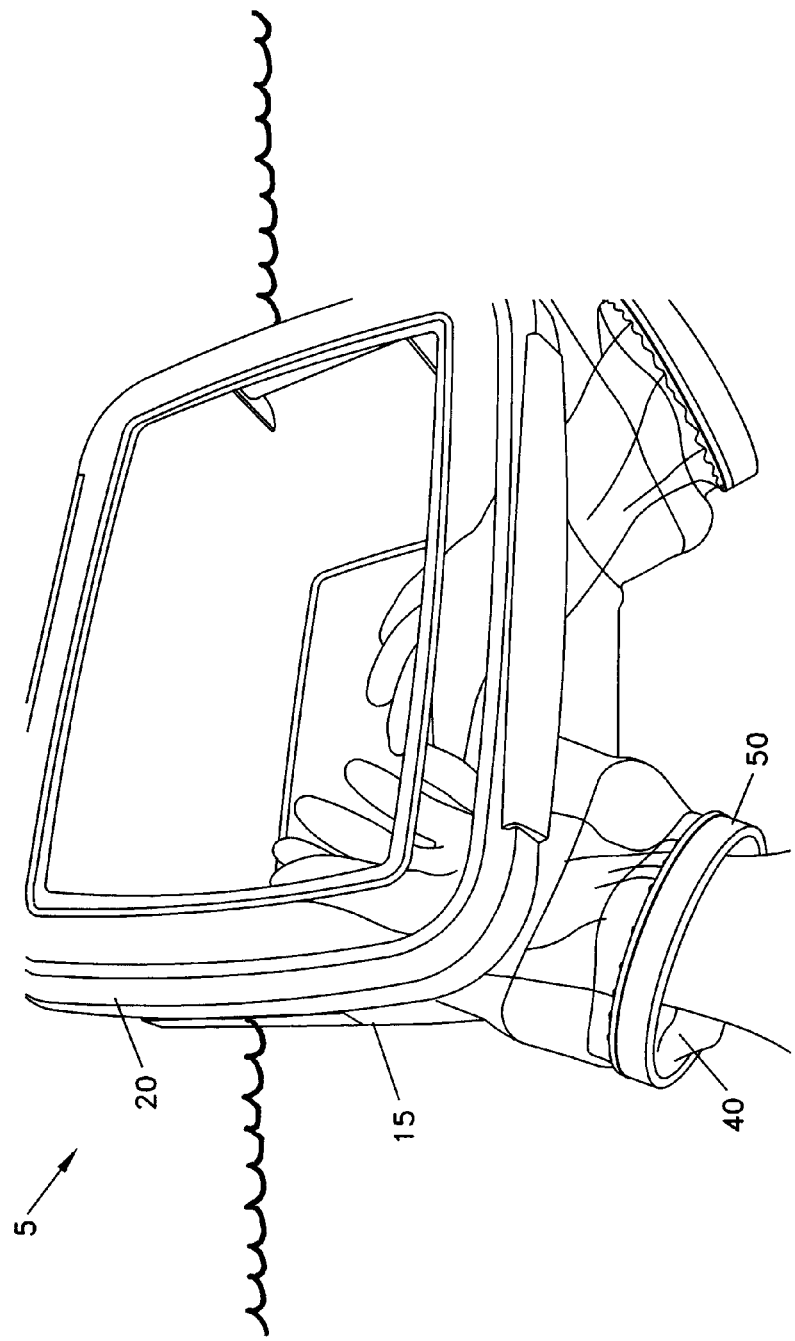
FIG. 30 is a schematic view showing the PRIB of FIGS. 1, 2, 3 and 4 floating in water.

Integrated into one or more locations on main housing 10 of PRIB 5 are ports 35 (FIG. 18) into which disposable rubber gloves 40 or other disposable elements are attached in airtight/watertight continuity with isolation bay 30. Ports 35 are designed with features that allow gloves 40 or other disposable members 40 to be rapidly and easily changed, e.g., such as when a glove becomes torn or damaged. By way of example but not limitation, ports 35 may comprise a rim 45 (FIG. 18) having threads 60 thereon. Gloves 40 are inserted into ports 35 and their cuffs are stretched over rims 45. Then ring caps 50 are screwed over the cuffs of the gloves, whereby to secure gloves 40 inside ports 35. On account of this construction, the user may pass their hand (FIG. 4) into the interior of PRIB 5 so as to manipulate objects within PRIB 5 while maintaining isolation therefrom. Thus it will be seen that PRIB 5 is designed so that the airtight/watertight nature of the connection to isolation bay 30 is maintained after changing disposable rubber gloves 40 or other disposable elements 40.

In some iterations of PRIB 5, one or two ports 35 with disposable gloves 40 attached allow an individual to insert one or two hands into the isolation bay of main housing 10 and manipulate an isolated item while visualizing the item through the PRIB's transparent lid 20. In other iterations of the PRIB, disposable elements 40 are designed to allow insertion of part or all of one or more fingers, or the distal half of one or both hands, but are not true "gloves" in the full sense of the word. In still other iterations, disposable elements 40 comprise one or more extended gloves that allow the hand, wrist, forearm, and elbow to be inserted into the isolation bay. And in still other iterations, multiple sets of disposable elements 40 allow two or more individuals to insert fingers, hands, and/or arms into a common isolation bay to allow for coordinated efforts between two or more individuals as may be required in some games or other endeavors. In other iterations, disposable elements 40 are designed to accommodate tools, implements, feet, or other appendages that could be used to manipulate items in the isolation bay 30 of PRIB 5.

Different versions of PRIB 5 are designed for dedicated purposes to maximize function for a given task while optimizing size and geometry. Examples of uses for which such dedicated PRIBs are designed include, but are not limited to the following constructions.

PRIB for Holding Books, Magazines and/or other Paper Products

Several varieties of PRIB 5 may be configured to hold books, magazines, and/or other paper products.

In one embodiment, PRIB 5 is configured to isolate a paperback or similar size book so as to allow the book to be read in a tub or sauna, at the beach, in or by the pool, in the rain or other hostile environments, while protecting the book from cumulative water and/or other damage. Disposable elements 40 allow the pages to be turned effortlessly, and transparent lid 20 allows the book to be read through the PRIB. An ultra-bright white LED or other light (not shown) may also be incorporated into the PRIB so as to facilitate visualization. The PRIB geometry and sizing keeps the book open to the desired page (i.e., by prohibiting the book from closing without opening the lid), thereby providing additional functionality. The PRIB may be designed to be propped up on one's knees in the tub. Alternatively, the PRIB could have a floating base and/or a beveled isolation bay which holds the book at the optimal angle for reading in the water or other environment.

In another embodiment, PRIB 5 is configured to isolate a larger book for reading in the tub or sauna, at the beach, by the pool, in the rain, or other hostile environments, while protecting the book from cumulative water and/or other damage. Disposable elements 40 allow the pages to be turned effortlessly, and transparent lid 20 allows the book to be read through the PRIB. An ultra-bright white LED or other light (not shown) may also be incorporated into the PRIB so as to facilitate visualization. The PRIB geometry and sizing keeps the book open to the desired page (i.e., by prohibiting the book from closing without opening the lid), thereby providing additional functionality. The PRIB may be designed to be propped up on one's knees in the tub. Alternatively, the PRIB could have a floating base and/or a beveled isolation bay which holds the book at the optimal angle for reading in the water or other environment.

In another embodiment, PRIB 5 is configured to isolate a book of antiquarian or historical value from cumulative stress and deterioration while being handled by users, and provide a non-stress, non-hostile environment for the book. The book is protected by the PRIB from atmospheric moisture, skin oil, and unanticipated spills, sneezes and/or other misadventures.

In another embodiment, PRIB 5 is configured to hold a crossword puzzle or other work or game book, along with a pen, pencil, marker or other writing instrument, so as to allow the crossword puzzle or other work or game book to be used as intended in the tub, in the sauna, at the beach, by the pool, in the rain, or other hostile environments, while protecting the crossword puzzle or other work or game book from cumulative water and/or other damage.

In another embodiment, PRIB 5 is configured to isolate a coloring book or other game or workbook, along with multiple colored markers, pens, paints or crayons, thus allowing the coloring book to be used as intended while protecting the environment from stains and marking by the pens. This is of value with small children and/or others for whom careful control of permanent markers and/or other potentially destructive writing and/or drawing implements is challenging. By virtue of the airtight and watertight construction of the PRIB, the markers or pens would never be lost and would dry out much more slowly if left uncapped than they otherwise would if left in the open air. The caps for the markers or pens may be permanently affixed to the inner aspect of the isolation bay in order to keep the markers or pens organized between uses or during use.

The isolation bay may also have childproof features that prevent a child from opening the isolation bay without adult help. Several coloring books or workbooks may be placed in the isolation bay at once, and the child could rearrange them to get to the desired book, open to the desired page, and color with markers, all within the PRIB isolation bay, without risk of marking or staining the environment.

A PRIB of this type is valuable and entertaining for children during long drives in the car, where losing caps and markers and avoiding destructive marker mishaps is challenging. Another potential use is in a pediatrician's waiting room, where a fresh pair of disposable gloves allows a toddler or child to color without risk of transmission of infectious agents, avoids marker stains, avoids lost markers and caps, helps prevent markers from drying out, etc.

In an alternative embodiment, PRIB 5 may be positioned on an easel (not shown) and could house a large tablet of paper held vertically and finger-paints. The paints would not dry out, and the child's clothes and the environment are isolated and protected from artistic misadventure.

PRIB for Use in the Kitchen

Other varieties of PRIB could be designed for food preparation in the kitchen so as to facilitate clean up after messy tasks and/or to isolate the user from noxious stimuli.

Figure 5:
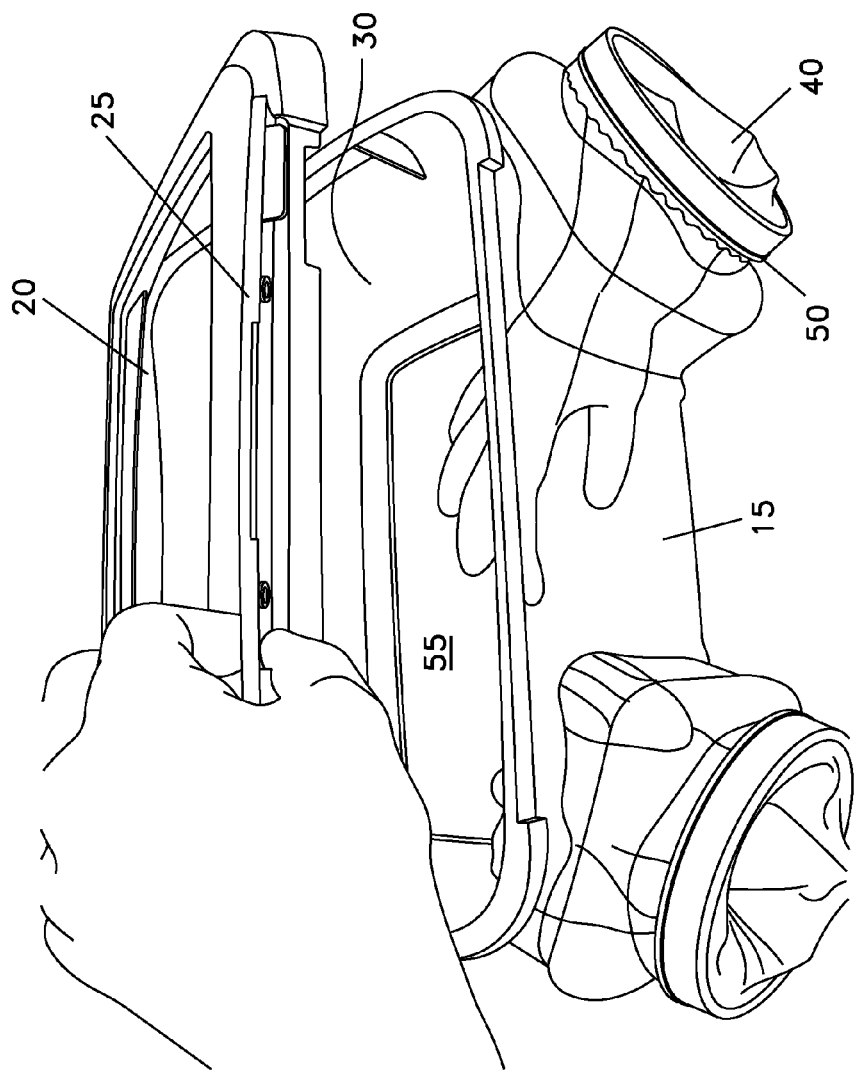
FIG. 5 is a schematic view showing the PRIB of FIGS. 1, 2, 3 and 4, except with the lid opened.
Figure 6:
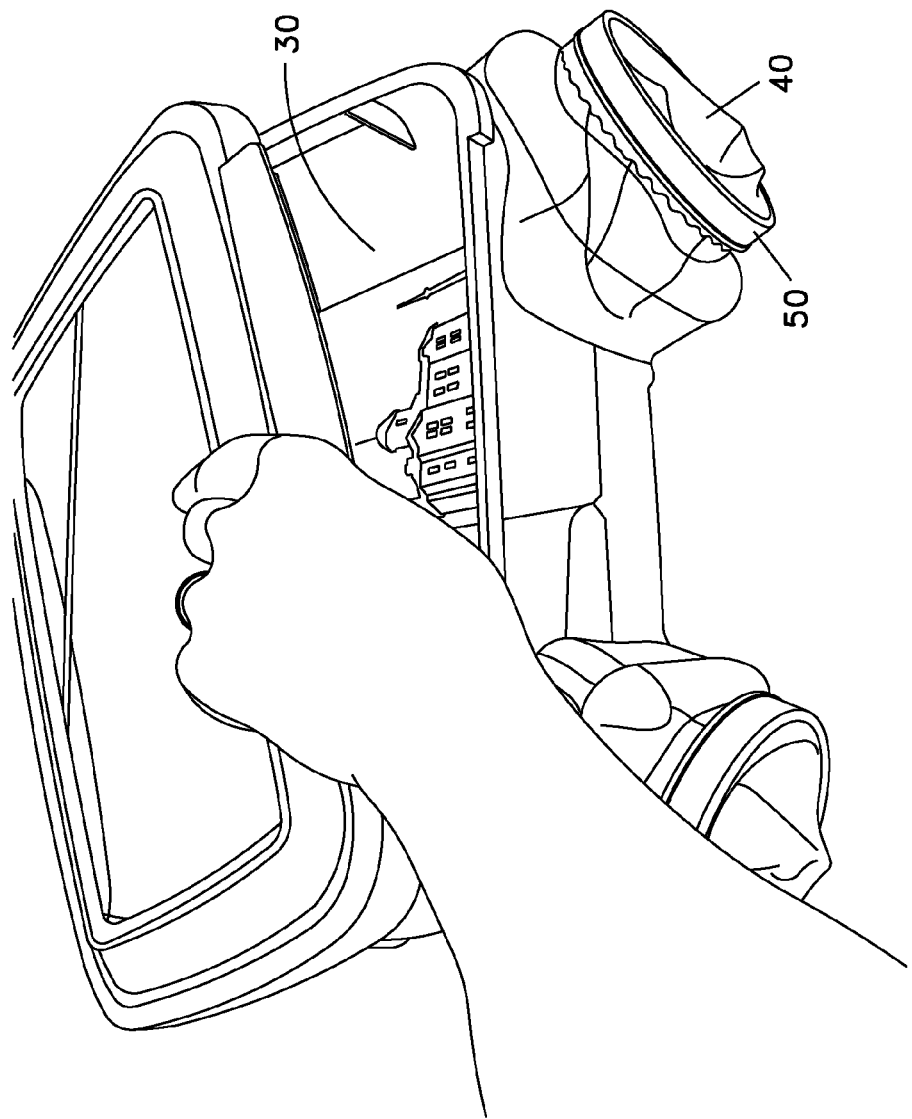
FIG. 6 is a schematic view showing the PRIB of FIGS. 1, 2, 3 and 4, except with the lid opened.
Figure 7:
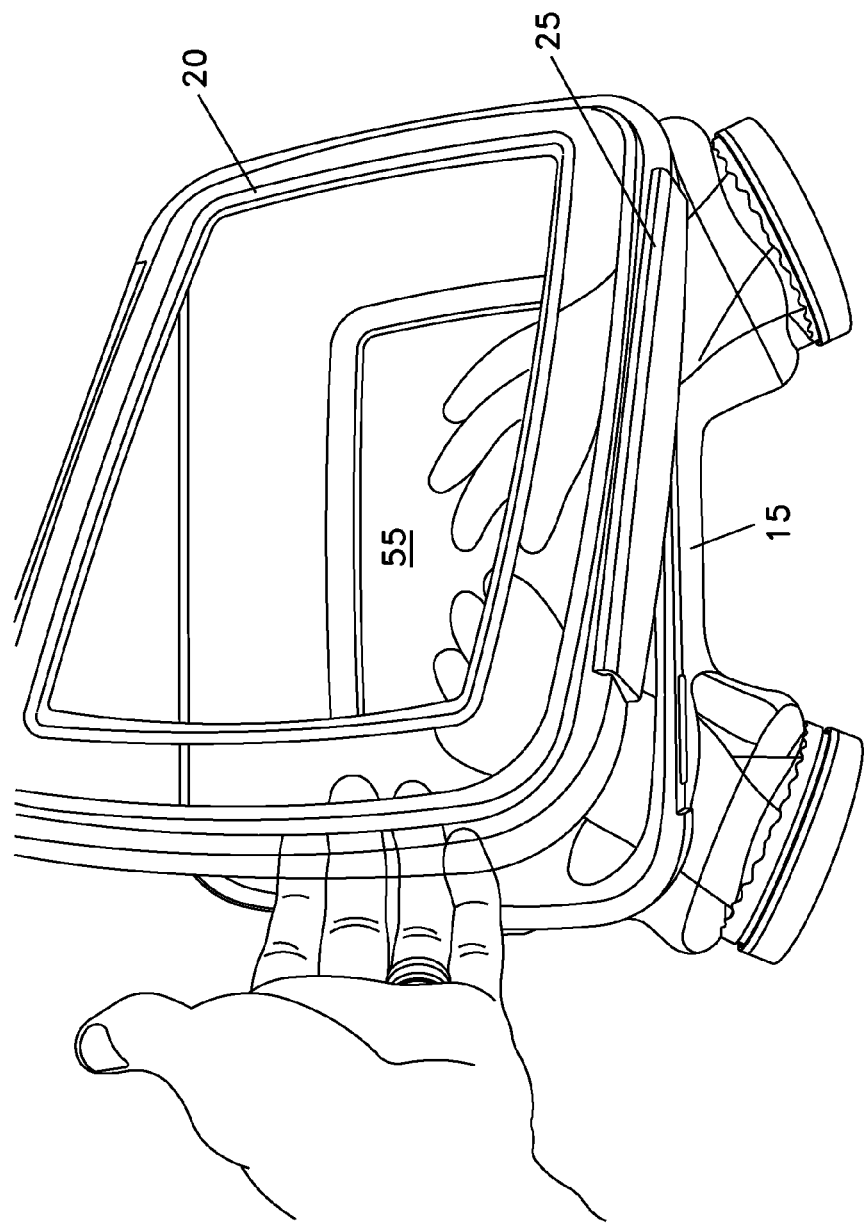
FIG. 7 is a schematic view showing the PRIB of FIGS. 1, 2, 3 and 4, except with the lid opened.
Figure 8:
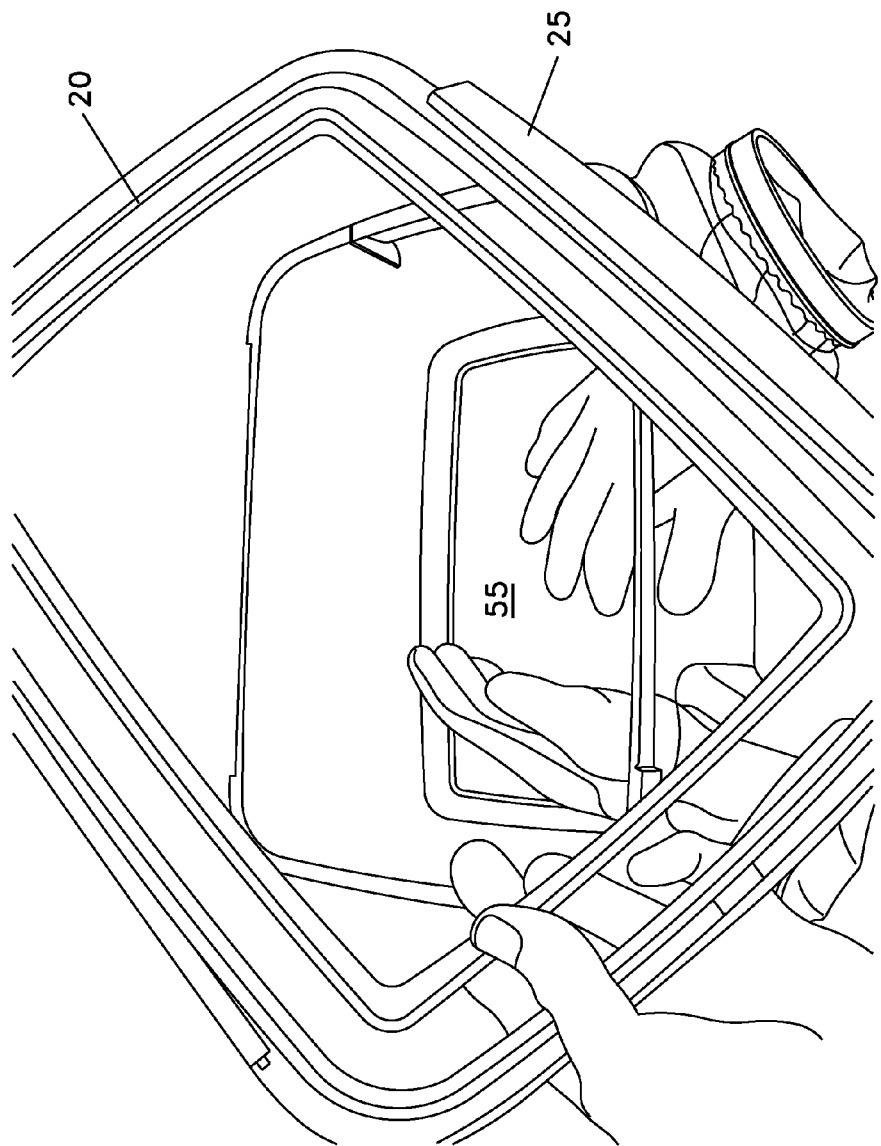
FIG. 8 is a schematic view showing the PRIB of FIGS. 1, 2, 3 and 4, except with the lid opened.
Figure 9:
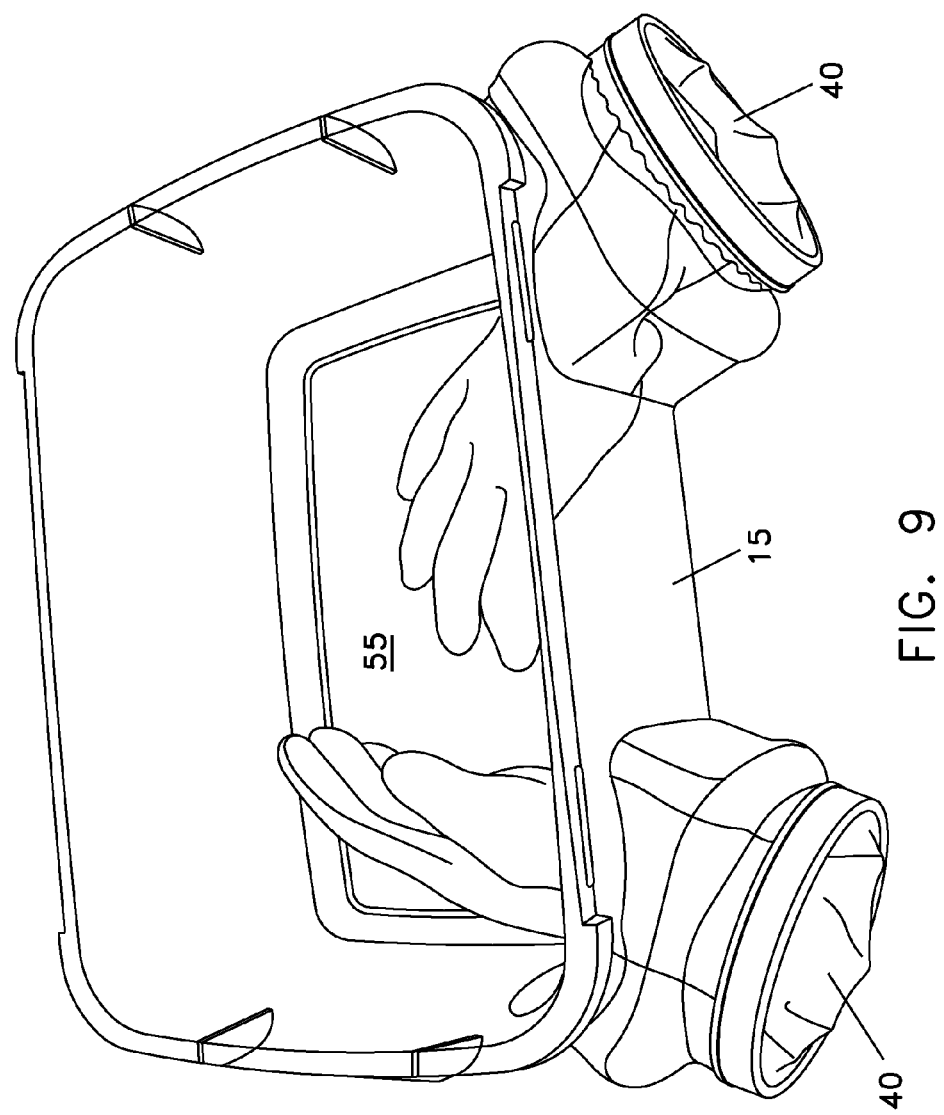
FIG. 9 is a schematic view showing the PRIB of FIGS. 1, 2, 3 and 4, except with the lid removed.
Figure 10:
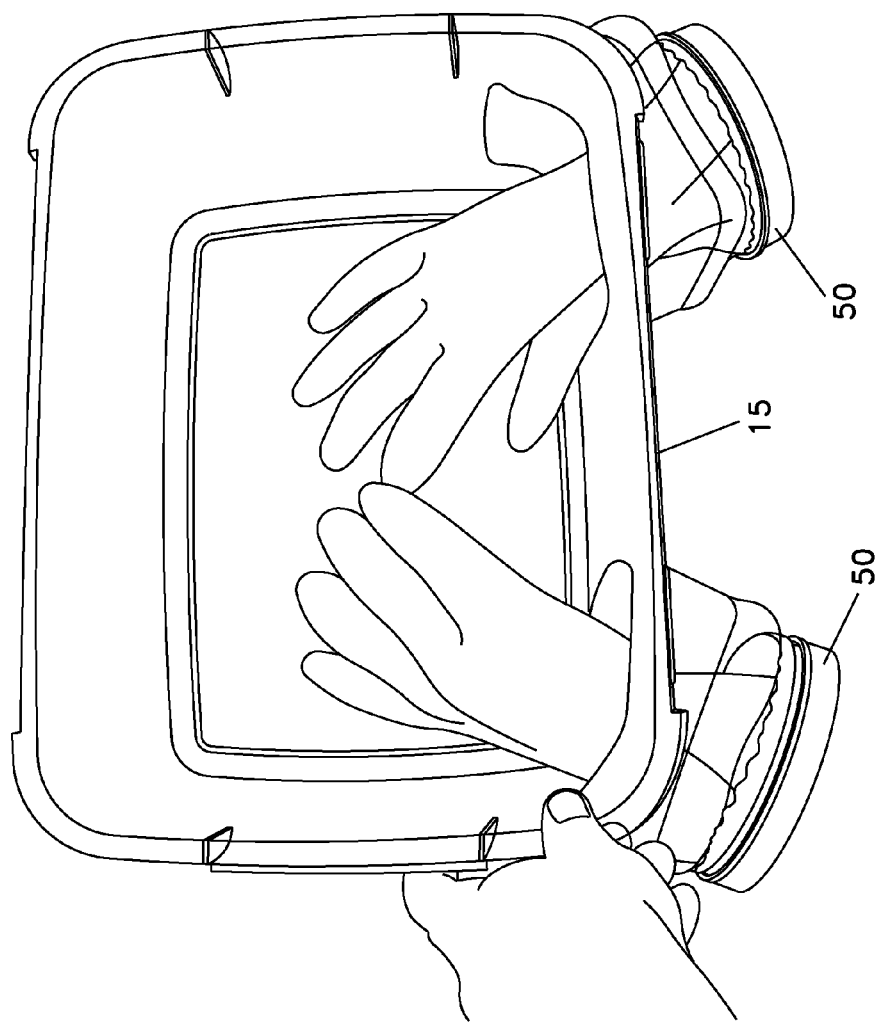
FIG. 10 is a schematic view showing the PRIB of FIGS. 1, 2, 3 and 4, except with the lid removed.
Figure 11:
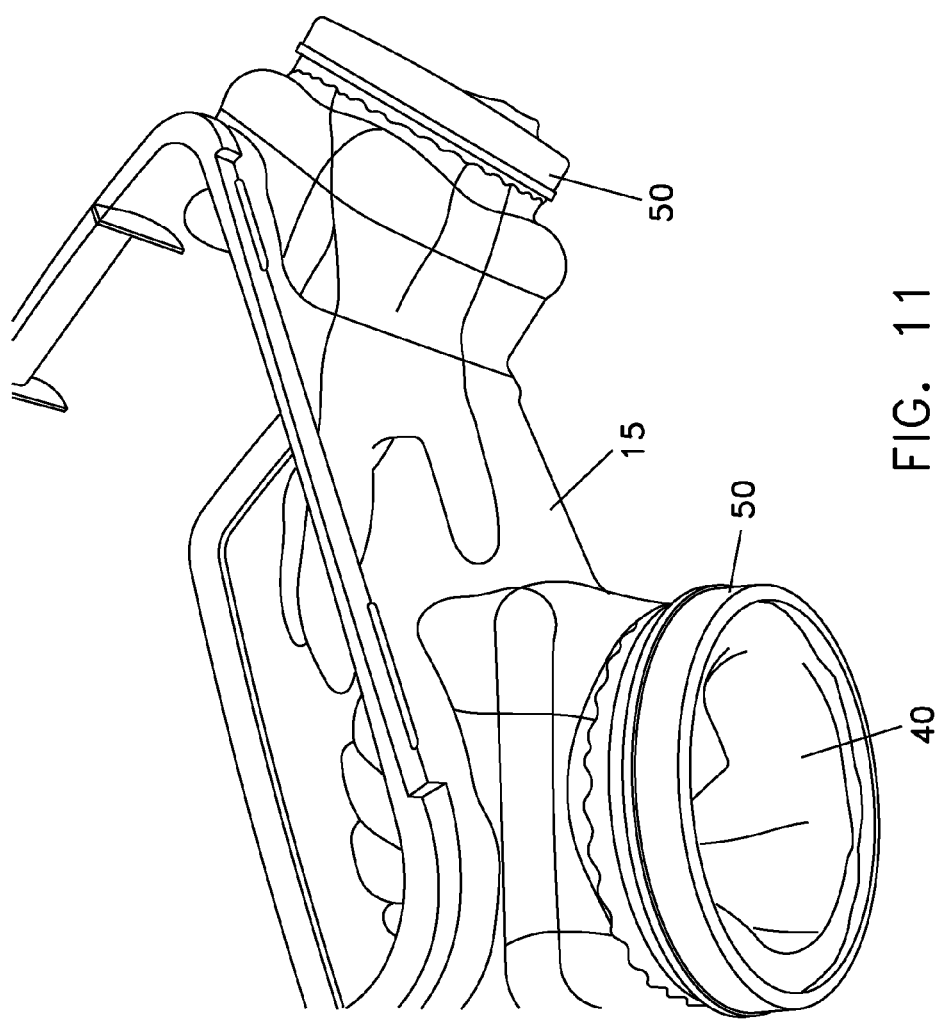
FIG. 11 is a schematic view showing the PRIB of FIGS. 1, 2, 3 and 4, except with the lid removed.
Figure 12:
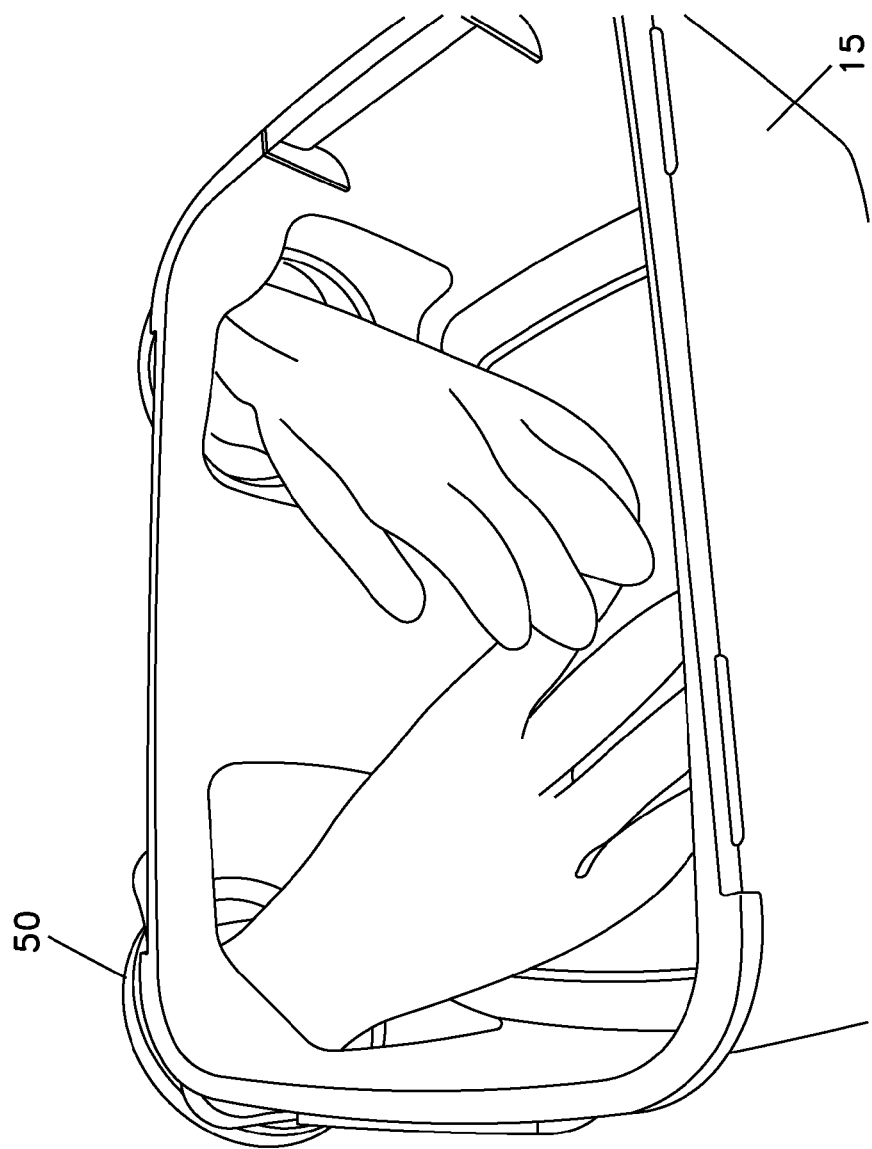
FIG. 12 is a schematic view showing the PRIB of FIGS. 1, 2, 3 and 4, except with the lid removed.
Figure 13:
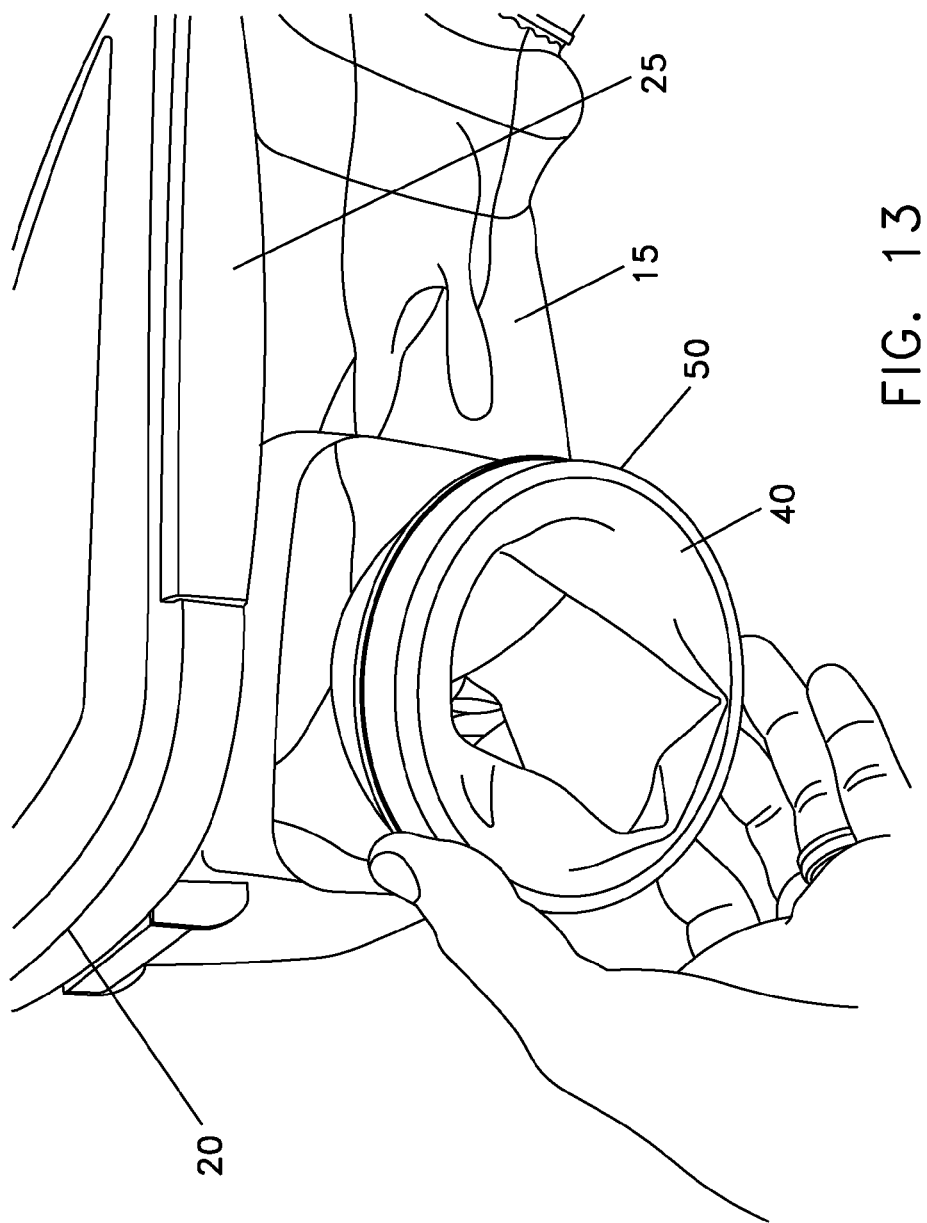
FIG. 13 is a schematic view showing details of the main housing, ports, and disposable gloves of the PRIB shown in FIGS. 1, 2, 3 and 4.
Figure 14:
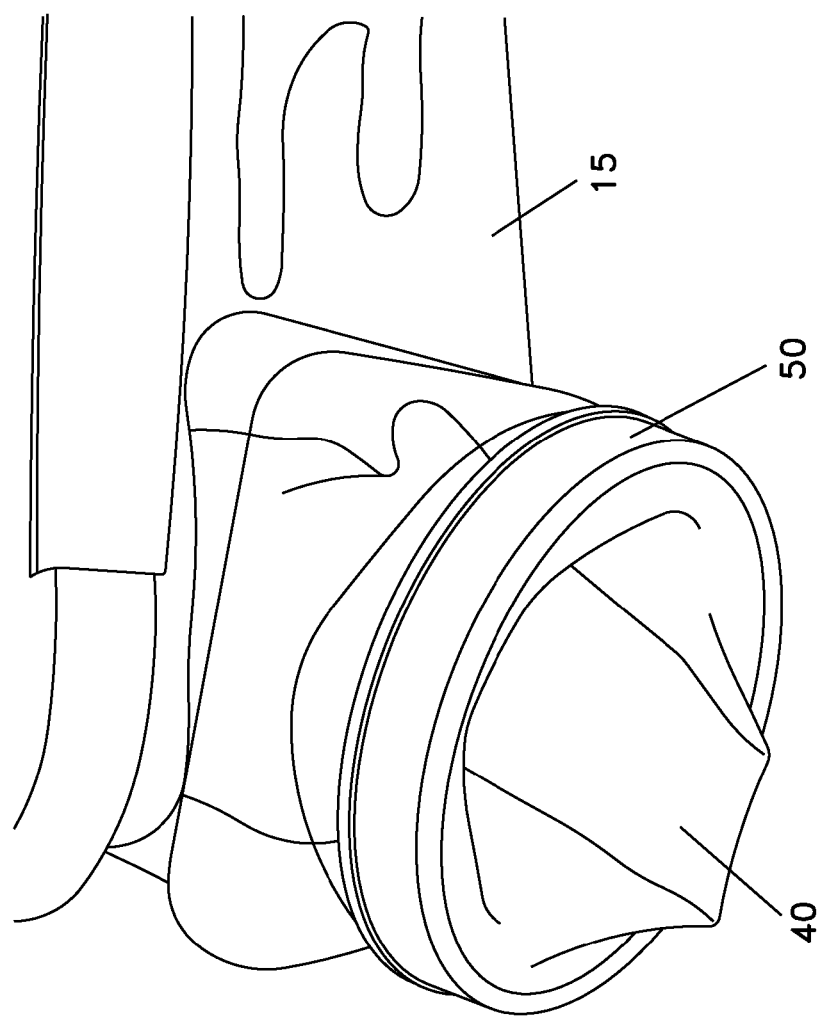
FIG. 14 is a schematic view showing details of the main housing, ports, and disposable gloves of the PRIB shown in FIGS. 1, 2, 3 and 4.
Figure 15:
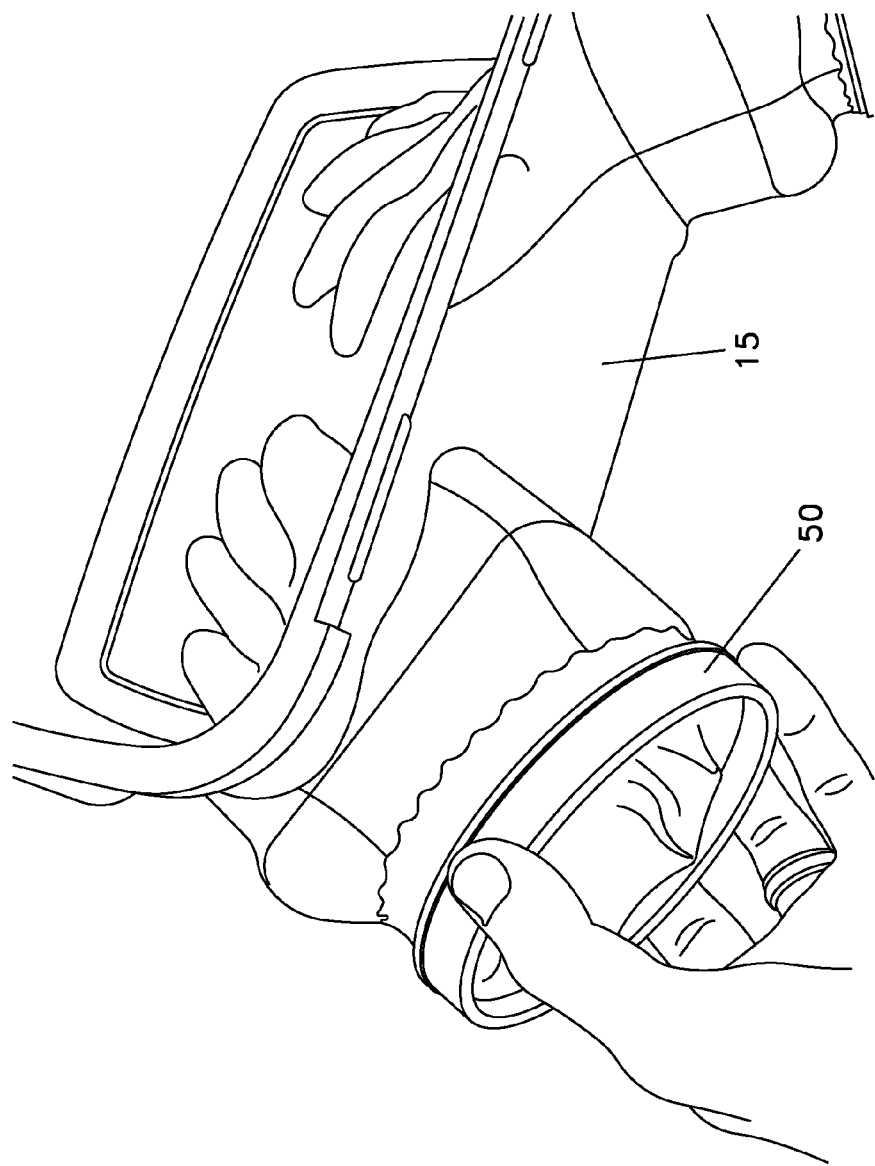
FIG. 15 is a schematic view showing details of the main housing, ports, and disposable gloves of the PRIB shown in FIGS. 1, 2, 3 and 4.
Figure 16:
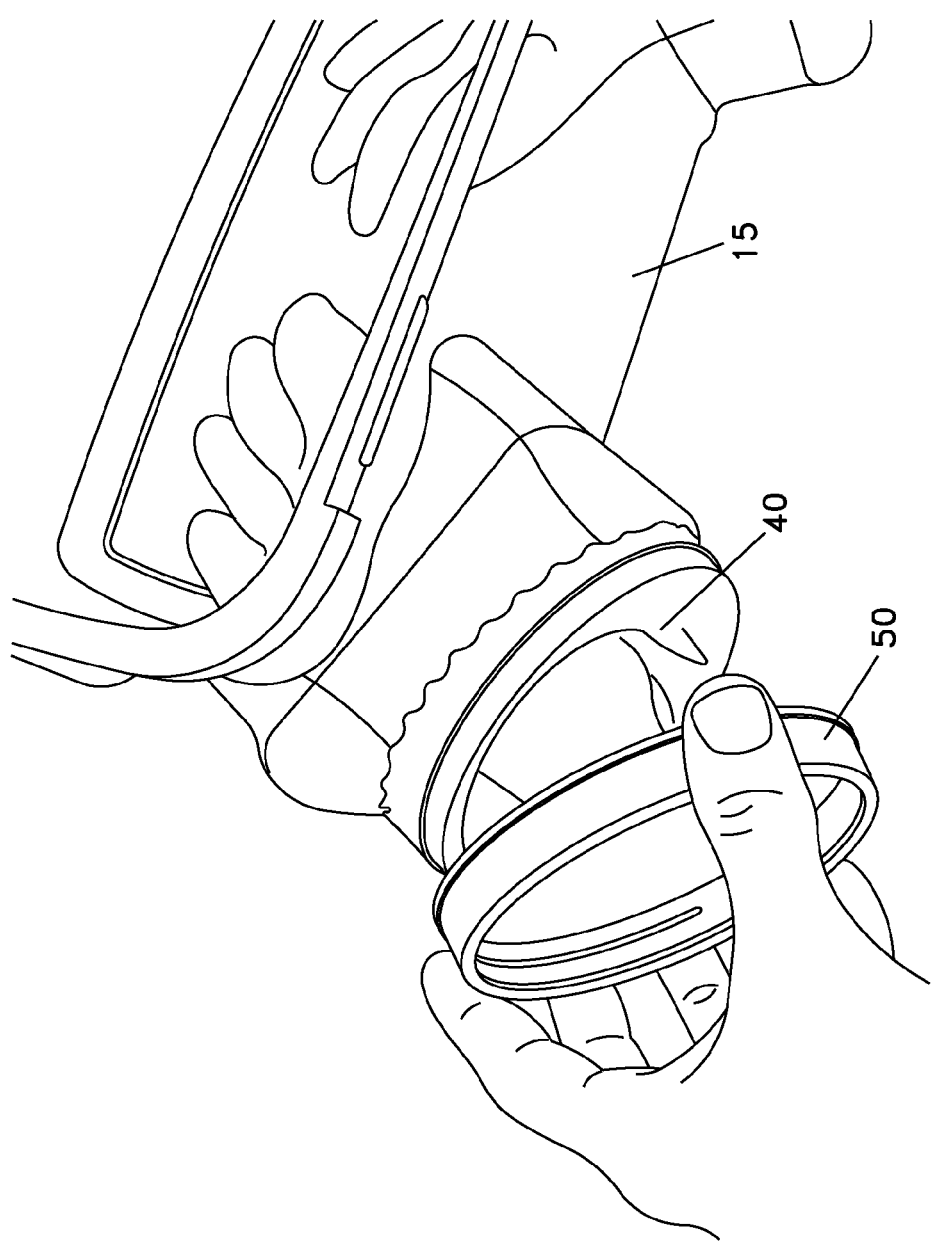
FIG. 16 is a schematic view showing details of the main housing, ports, and disposable gloves of the PRIB shown in FIGS. 1, 2, 3 and 4.
Figure 17:
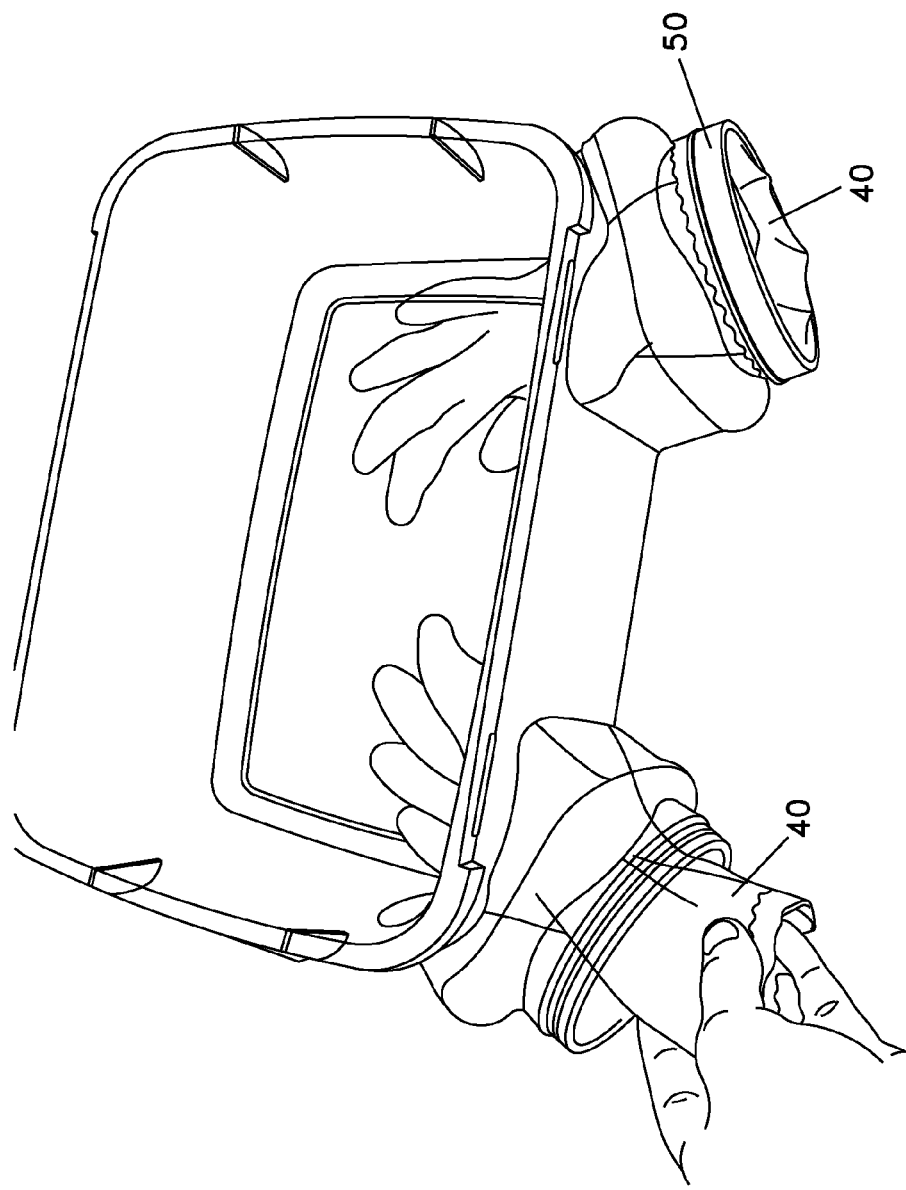
FIG. 17 is a schematic view showing details of the main housing, ports, and disposable gloves of the PRIB shown in FIGS. 1, 2, 3 and 4.

In one embodiment of the present invention, PRIB 5 is designed for cutting or dicing onions. In this embodiment, base 55 (FIG. 5) of isolation bay 30 may be made of materials, and configured like, a cutting board and a knife or other cutlery may be placed in the box alongside one or more onions, cloves of garlic, or other noxious food. The airtight and watertight lid of the PRIB may then be secured, with the onions and knife in the isolation bay. The onions are then peeled, sliced, and diced inside the enclosure of the PRIB. The PRIB contains the noxious fumes and helps keep the diced onions fresh until such time as they are needed.

In another embodiment of the present invention, PRIB 5 is configured to prepare freshly caught fish, oysters, clams, squid, shrimp, crabs and the like, or for skinning and/or cleaning small game. With the PRIB, the scales, shells, bones, viscera and such could be readily contained and disposed of with effectively no mess to clean up.

In another embodiment of the present invention, PRIB 5 may be designed for marinating or breading food. By way of example, it is sometimes desirable to roll meat, poultry, or fish in flour, breadcrumbs, cornmeal, or other granular foodstuff. Similarly, it is sometimes desirable to coat food in marinades or other sauces for prolonged periods of time. A PRIB of this variety would allow the user to place the meat, poultry, or fish in the isolation bay, along with the breading or sauce and a brush or other appliance to facilitate the even dispersal of the coating. The food may remain in the isolation bay with the marinade for prolonged periods of time, as is done with conventional marinade processes. With a PRIB of this variety, one is able to reposition the food that is being marinated or breaded, facilitating even dispersal, without touching either the food or sauce. Accordingly this PRIB minimizes mess, facilitates clean-up, and allows the procedure to be performed, in some cases even without taking the PRIB out of the refrigerator.

PRIB for Use in a Home Shop

In another embodiment of the present invention, a PRIB may be optimized to facilitate projects in the home shop, including cleaning parts or removing glue or paint with noxious solvents or thinners, painting or coating objects in a dust-free environment, or assembling multiple small components without risk of dropping and/or loosing them.

PRIB with Multiple Ports

Other PRIBs are designed with multiple ports 35 so as to allow multiple individuals to play cards or other games in the tub, in the sauna, at the beach, by the pool, in the rain or other hostile environments.

One iteration allows a plurality of players to each insert two hands into a large floating circular PRIB so as to allow "pool poker" to be played. The isolation bay is loaded with chips and cards and then the lid is sealed. The entire game is played within the watertight and airtight isolation bay. A PRIB of this type also shelters cards from the wind so as to facilitate poker at the beach and/or other challenging environments.

Some of the unique and patentable features of the novel PRIBs include their low cost, ease of use, portability, and dedicated design for a specific task. Features that maximize these aspects of function include a low-cost, injection-molded construction, small size and the incorporation of inexpensive, easily replaced, disposable gloves. Unlike most currently available isolation hoods or tents, which are intended for use with radioactive materials, biohazards, infectious material, carcinogens, poisons, or caustic substances, etc, the ramifications of device failure with the PRIBs are substantially less. As such, the gloves can be inexpensive, disposable gloves 40 that are readily available, and which can be easily replaced as needed. Alternatively, some types of PRIBs may require dedicated disposable members 40, e.g., either full arm-length gloves, partial hand gloves, or other geometries. These disposable elements 40 could be very cheaply fabricated due to the intended use and limited consequences of breach or leak.

The PRIB of the present invention provides a fast, simple and reliable approach for replaceably attaching the gloves to the PRIB, e.g., a threaded neck for receiving the wrist of the glove, and a threaded rim for capturing the wrist of the glove to the threaded neck.

Furthermore, because the isolation bay is watertight/airtight, it could be manipulated during closure of the lid to force an egress of air, such that after the forced egress of air is completed, the sealed isolation bay of the PRIB is at a sub-atmospheric pressure. Thus, the PRIB can be "burped" like a Tupperware container. The "burping" causes the disposable gloves or other disposable elements to inflate with room air or water (whatever was outside the box), which facilitates insertion and removal of one's hands while accessing the contents of the PRIB. By way of example but not limitation, the PRIB can be formed out of a flexible plastic such that the PRIB can have its isolation chamber reduced in size (e.g., by pressing one or more walls inwardly), closing the lid, and then allowing the isolation chamber to return to its normal size (e.g., by releasing the inward pressure on the one or more walls). The arrangement will effectively cause the isolation chamber to have an interior air pressure which is lower that the exterior air pressure, so that the gloves will be automatically inflated.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A portable reverse isolation box (PRIB) for protecting an object from an environment and/or for protecting a user from said object, the PRIB comprising:
   a closed bottom and an open top;
   a sidewall extending between said closed bottom and said open top, and defining an interior, said sidewall comprising:
      a continuous rear wall;
      a front wall opposite said rear wall, said front wall having:
         a first rounded corner formed along a first end;
         a second rounded corner formed along a second end;
         a first side extending between said first rounded corner and said rear wall;
         a second side opposite said first side and extending between said second rounded corner and said rear wall;
   a removable lid comprising:
      a transparent top portion;
      a rounded shoulder surrounding said top portion;
      an outer flange having a lock for selectively sealing said interior to form an airtight and watertight isolation bay;
   a first port formed along said first rounded corner, said first port comprising:
      a first tubular projection having:
         a distal end having a first threaded annular rim with an exterior edge defined along a first transverse axis,
         a proximal end projecting outward from said first side and said front wall, and
         a first longitudinal axis extending obliquely from said sidewall between the distal end and the proximal end;
   a first glove mounted in said first tubular projection in airtight and watertight continuity with said isolation bay,
   a first threaded ring engaging the first threaded annular rim and securing the first glove to the first tubular projection;
   a second port formed along said second rounded corner, said second port comprising:
      a second tubular projection having:
         a distal end having a second threaded annular rim with an exterior edge defined along a second transverse axis,
         a proximal end projecting outward from said second side and said front wall, and
         a second longitudinal axis extending obliquely from said sidewall between the distal end and the proximal end;
   a second glove mounted in said second tubular projection in airtight and watertight continuity with said isolation bay,
   a second threaded ring engaging the second threaded annular rim and securing the second glove to the second tubular projection;
   wherein said first and second gloves are capable of assuming a concave configuration permitting the user to manipulate said object within said isolation bay without opening said lid; and, said first and second gloves are each everted such that a portion of each glove respectively extends through each port and over each proximal end of each respective tubular projection;
   wherein said first longitudinal axis and said second longitudinal axis converge in an interior direction toward said isolation bay; and, said first transverse axis and said second transverse axis converge in an exterior direction along the front wall away from said isolation bay.

2. The portable reverse isolation box (PRIB) according to claim 1 further comprising a writing instrument and a writing medium disposed in the isolation bay.

3. The portable reverse isolation box (PRIB) according to claim 1 wherein the PRIB is disposed on an easel.

4. The portable reverse isolation box (PRIB) according to claim 1 further comprising reading material disposed in said isolation bay, wherein the isolation bay is beveled for displaying said reading material at an angle for optimal reading.

5. The portable reverse isolation box (PRIB) according to claim 1 wherein said first and second gloves are flexible and disposable.

6. The portable reverse isolation box (PRIB) according to claim 1 wherein said first and second gloves are formed from a rubber material.

7. The portable reverse isolation box (PRIB) according to claim 1 further comprising a food and a food implement disposed in the isolation bay.

8. The portable reverse isolation box (PRIB) according to claim 7 wherein the food implement is a knife.

9. The portable reverse isolation box (PRIB) according to claim 1 wherein said closed bottom and said sidewall are formed from a semi-rigid material.

10. The portable reverse isolation box (PRIB) according to claim 9 wherein said semi-rigid material comprises plastic.

11. The portable reverse isolation box (PRIB) according to claim 1 wherein said removable lid is formed from a semi-rigid material.

12. The portable reverse isolation box (PRIB) according to claim 11 wherein said semi-rigid material comprises plastic.

13. The portable reverse isolation box (PRIB) according to claim 1 further comprising a playing implement disposed in the isolation bay.

14. The portable reverse isolation box (PRIB) according to claim 13 wherein the playing implement is a game board.

15. The portable reverse isolation box (PRIB) according to claim 13 wherein the playing implement is a deck of playing cards.

* * * * *